US006211165B1

(12) United States Patent
Liang et al.

(10) Patent No.: US 6,211,165 B1
(45) Date of Patent: Apr. 3, 2001

(54) METHODS AND COMPOSITIONS FOR REDUCING ISCHEMIC INJURY OF THE HEART BY ADMINISTERING ADENOSINE RECEPTOR AGONISTS AND ANTAGONISTS

(75) Inventors: Bruce T. Liang, Merion Station, PA (US); Kenneth A. Jacobson, Silver Springs, MD (US)

(73) Assignees: The Trustees of the University of Pennsylvania, Philadelphia, PA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/423,129

(22) PCT Filed: May 8, 1998

(86) PCT No.: PCT/US98/09031

§ 371 Date: Nov. 5, 1999

§ 102(e) Date: Nov. 5, 1999

(87) PCT Pub. No.: WO98/50047

PCT Pub. Date: Nov. 12, 1998

Related U.S. Application Data

(60) Provisional application No. 60/046,030, filed on May 9, 1997, and provisional application No. 60/061,716, filed on Oct. 10, 1997.

(51) Int. Cl.$^7$ .................................................... A61K 31/70
(52) U.S. Cl. ................................................................. 514/46
(58) Field of Search ................................................... 514/46

(56) References Cited

U.S. PATENT DOCUMENTS 4,657,897 * 4/1987 Bristol et al. .......................... 514/47

FOREIGN PATENT DOCUMENTS 2264949    9/1993  (GB) .

OTHER PUBLICATIONS

Suhaib M. Siddiqi, et al. Search for New Purine–and Ribose–Modified Adenosine Analogues as Selective Agonists and Antagonists at Adenosine Receptors. Journal of Medicinal Chemistry. (Mar. 31, 1995) 1174–1188.
Kenneth A. Jacobson, et al. Structure–Activity Relationships of 9–Alkyladenine and Ribose–Modified Adenosine Derivatives at Rat $A_3$ Adenosine Receptors. Journal of Medicinal Chemistry. (May 12, 1995) 1711–1719.
Philip J.M. Van Galen, et al. A Binding Site Model and Structure–Activity Relationships for the Rat $A_3$ Adenosine Receptor. Molecular Pharmacology. (1994) 45:1101–1111.
Kenneth A. Jacobson, et al. A Role for Central $A^3$–Adenosine Receptors Mediation of Behavioral Depressant Effects. Federation of European Biochemical Societies. (Dec. 1993) 336,1:57–60.

Qun–Yong Zhou, et al. Molecular Cloning and Characterization of an Adenosine Receptor: The $A_3$ Adenosine Receptor. Proc. Natl. Acad. Sci. USA (Aug. 1992) 89:7432–7436.
Vickram Ramkumar, et al. The $A_3$ Adenosine Receptor is the Unique Adenosine Receptor Which Facilitates Release of Allergic Mediators in Mast Cells. The Journal of Biological Chemistry. (Aug. 15, 1993) 268,23:16887–16890.
Suhaib M. Siddiqu, et al. Comparative Molecular Field Analysis of Selective $A_3$ Adenosine Receptor Agonists. Bioorganic & Medicinal Chemistry. (1995) 3,10: 1331–1343.
Timothy M. Palmer ,et al. Differential Interaction with and Regulation of Multiple G–Proteins by the Rat $A_3$ Adenosine Receptor. The Journal of Biological Chemistry. (Jul. 14, 1995) 270,28:1695–16902.
John R. Fozard, et al. The Cardiovascular Effects of Selective Adenosine $A_1$ and $A_2$ Receptor Agonists in the Pihted Rat: No Role for Glibenclamide–Sensitive Potassium Channels. Nauyn–Schmiedeberg s Archives of Pharmacology. (1993) 347:192–196.
Guang S. Liu, et al. Evidence That the Adenosine $A_3$ Receptor May Mediate the Protection Afforded by Preconditioning in the Isolated Rabbit Heart. Cardiovascular Research. (1994) 28:1057–1061.
B.T. Liang. Co–Activation of Adenosine $A_1$ and $A_3$ Receptors. Acknowledgment 23–24 & 2 sheets of figures. (No date available).
Jennifer Strickler, et al. Direct Preconditioning of Cultured Chick Ventricular Myocytes. J. Clin. Invest. (Oct. 19660 98,8:1773–1779.
Bruce T. Liang. Direct Preconditioning of Cardiac Ventricular Myocytes Via Adenosine $A_1$ Receptor and $K_{ATP}$ Channel. The American Physiological Society. (1996) 0363–6135, H1769–H1777.
Kenneth A. Jacobson, et al. $A_3$–Adenosine Receptors: Design of Selective Ligands and Therapeutic Prospects. Drugs of the Future. (1995) 20(7): 689–699.
Michel C. Maillard, et al. Adenosine Receptor Prodrugs: Synthesis and Biological Activity of Derivatives of Potent, $A_1$–Selective Agonists. Journal of Pharmaceutical Sciences. (Jan. 1994) 83,1:46–53.
Pier Giovanni Baraldi, et al. Novel $N^6$–(Substituted–Phenylcarbamoyl) Adenosine–5'–Uronamides as Potent Agonists for $A_3$ Adenosine Receptors. Journal Of Medicinal Chemistry. (1996) 39:802–806.

(List continued on next page.)

Primary Examiner—Raymond Henley, III
(74) Attorney, Agent, or Firm—Dann, Dorman, Herrell and Skillman

(57) ABSTRACT

Compositions and methods for reducing or preventing ischemic damage of the heart are disclosed. A preferred embodiment of the invention comprises the simultaneous administration of specific A3/A1 receptor agonists, to patients suffering from ischemic damage or at risk for the same. In yet another embodiment of the invention, a binary conjugate which acts as an agonist for the A3 receptor and an antagonist at the A2a receptor, is administered to reduce or prevent ischemic damage to the heart.

60 Claims, 30 Drawing Sheets

OTHER PUBLICATIONS

Dag K.J.E. Von Lubitz. Neurodegenerative Disorders and Treatment With Selective Agents Acting at $A_1$ and $A_3$ Receptors: A Problem or a Bright Future? "$5^{th}$ International Symposium on Adenosine and Adenine Nucleotides." 1 sheet of Abstract (No date available).

Yangmee Shin, et al. Activation of Phosphoinositide Breakdown and Elevation of Intracellular Calcium in a Rat RBL–2H3 Mast Cell Line by Adenosine Analogs: Involvement of $A_3$–Adenosine Receptors? Drug Development Research (1996) 39:36–46.

Erno A. Van Schaick, et al. Hemodynamic Effects and Histamine Release Elicited by the Selective Adenosine $A_3$ Receptor Agonist 2–C1–Ib–Meca in Conscious Rats. European Journal of Pharmacology. (1996) 308:311–314.

Yao Yao, et al. Adenosine $A_3$ Receptor Agonists Protect HL–60 and U–937 Cells From Apoptosis Inducedby $A_3$ Antagonists. Biochemical and Biophysical Research Communications. (1997) 232:317–322.

Dag K.J.E. Von Lubitz, et al. Postischemic Administration of Adenosine Amine Congener (ADAC): Analysi8s of Recovery in Gerbils. European Journal of Pharmacology. (1996) 316:171–179.

Hea O. Kim, et al. 2–Substitution of $N^6$–Benzyladenosine–5'–Uronamides Enhances Selectivity for $A_3$ Adensone Receptors. Journal of Medicinal Chemistry. (Oct. 14, 1994) 3614–3621.

Carola Gallo–Rodriguez, et al. Structure–Activity Relationships of $N^6$–Benzyladenosine–5'–Uronamides as $A_3$–Selective Adenosine Agonists. Journal of Medicinal Chemistry. 37,5: 636–646 (1994).

Hea Ok Kim, et al. Selective Ligands for Rat A3 Adenosine Receptors: Structure–Activity Relationships of 1,3–Dialkylxanthine 7–Riboside Derivatives. Journal of Medicinal Chemistry. (Nov. 11, 1994) 4020–4030.

\* cited by examiner

* significantly different from those determined in the presence of CGS21680

Derivatization of $A_1$ selective agonist for coupling to amine-derivatized $A_3$ agonist

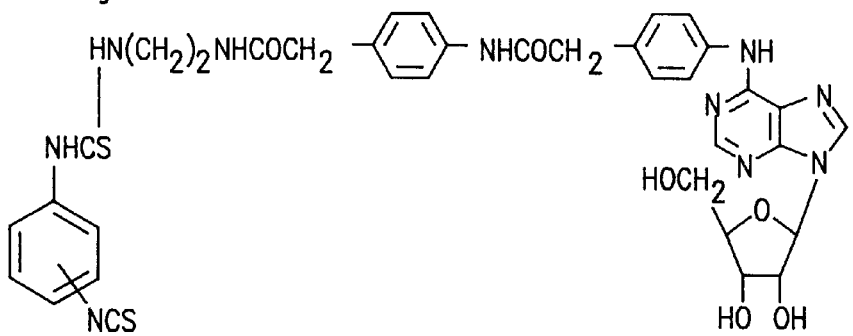

m- and p-DITC-ADAC

Derivatization of $A_3$ selective agonists

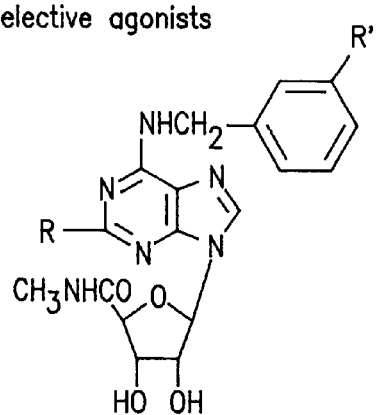

R'= C-CCH$_2$NHR"; R=H, Cl
for coupling to isothiocaynates or carboxylic acids;
R"=H, COCH(R''')NH$_2$[D-or L-amino acid],
for coupling to amines:
R"=CSNHC$_6$H$_4$-NCS (p-or m-)
COCH(R''')NHCSNHC$_6$H$_4$-NCS (p-or m-)
as $A_3$ agonists for exploring SAR:
R" =COCH$_3$, COCH(R''') NHCOOC(CH$_3$)$_3$[Boc-D-or L- amino acid],
R''' = any naturally occurring amino acid

FIG. 10A

Synthesis of binary conjugate with extended linker

Synthesis of binary conjugate with short linker

```
                              20                           40
       *          *            *            *            *
AAG CTT GAT ATC GAA TTC CGC AGG ATG GTG CTT GCC TCG TGC CCC TTG 60                           80
  *            *            *            *            *
GTG CCC GTC TGC TGA TGT GCC CAG CCT GTG CCC GCC ATG CCG CCC TCC
                                                  M   P   P   S>

100                          120                          140
       *            *            *            *            *
ATC TCA GCT TTC CAG GCC GCC TAC ATC GGC ATC GAG GTG CTC ATC GCC
 I   S   A   F   Q   A   A   Y   I   G   I   E   V   L   I   A>

160                          180
       *            *            *            *            *
CTG GTC TCT GTG CCC GGG AAC GTG CTG GTG ATC TGG GCG GTG AAG GTG
 L   V   S   V   P   G   N   V   L   V   I   W   A   V   K   V>

200                          220                          240
       *            *            *            *            *
AAC CAG GCG CTG CGG GAT GCC ACC TTC TGC TTC ATC GTC TCG CTG GCG
 N   Q   A   L   R   D   A   T   F   C   F   I   V   S   L   A>

260                          280
       *            *            *            *            *
GTG GCT GAT GTG GCC GTG GGT GCC CTG GTC ATC CCC CTC GCC ATC CTC
 V   A   D   V   A   V   G   A   L   V   I   P   L   A   I   L>

300                          320
  *            *            *            *            *
ATC AAC ATT GGG CCA CAG ACC TAC TTC CAC ACC TGC CTC ATG GTT GCC
 I   N   I   G   P   Q   T   Y   F   H   T   C   L   M   V   A>

340                          360                          380
       *            *            *            *            *
TGT CCG GTC CTC ATC CTC ACC CAG AGC TCC ATC CTG GCC CTG CTG GCA
 C   P   V   L   I   L   T   Q   S   S   I   L   A   L   L   A>

400                          420
       *            *            *            *            *
ATT GCT GTG GAC CGC TAC CTC CGG GTC AAG ATC CCT CTC CGG TAC AAG
 I   A   V   D   R   Y   L   R   V   K   I   P   L   R   Y   K>

440                          460                          480
       *            *            *            *            *
ATG GTG GTG ACC CCC CGG AGG GCG GCG GTG GCC ATA GCC GGC TGC TGG
 M   V   V   T   P   R   R   A   A   V   A   I   A   G   C   W>

500                          520
       *            *            *            *            *
ATC CTC TCC TTC GTG GTG GGA CTG ACC CCT ATG TTT GGC TGG AAC AAT
 I   L   S   F   V   V   G   L   T   P   M   F   G   W   N   N>
```

FIG. 11A

```
            540                        560
       *     *            *             *            *
CTG AGT GCG GTG GAG CGG GCC TGG GCA GCC AAC GGC AGC ATG GGG GAG
 L   S   A   V   E   R   A   W   A   A   N   G   S   M   G   E>

580                 600                       620
      *                   *                         *
CCC GTG ATC AAG TGC GAG TTC GAG AAG GTC ATC AGC ATG GAG TAC ATG
 P   V   I   K   C   E   F   E   K   V   I   S   M   E   Y   M>

640                        660
             *                          *                    *
GTC TAC TTC AAC TTC TTT GTG TGG GTG CTG CCC CCG CTT CTC CTC ATG
 V   Y   F   N   F   F   V   W   V   L   P   P   L   L   L   M>

680                 700                       720
        *                   *                         *
GTC CTC ATC TAC CTG GAG GTC TTC TAC CTA ATC CGC AAG CAG CTC AAC
 V   L   I   Y   L   E   V   F   Y   L   I   R   K   Q   L   N>

740                        760
                  *                          *
AAG AAG GTG TCG GCC TCC TCC GGC GAC CCG CAG AAG TAC TAT GGG AAG
 K   K   V   S   A   S   S   G   D   P   Q   K   Y   Y   G   K>

780                 800
  *     *            *      *                  *
GAG CTG AAG ATC GCC AAG TCG CTG GCC CTC ATC CTC TTC CTC TTT GCC
 E   L   K   I   A   K   S   L   A   L   I   L   F   L   F   A>

820                 840                       860
  *                   *                         *
CTC AGC TGG CTG CCT TTG CAC ATC CTC AAC TGC ATC ACC CTC TTC TGC
 L   S   W   L   P   L   H   I   L   N   C   I   T   L   F   C>

880                        900
             *                          *                    *
CCG TCC TGC CAC AAG CCC AGC ATC CTT ACC TAC ATT GCC ATC TTC CTC
 P   S   C   H   K   P   S   I   L   T   Y   I   A   I   F   L>

920                 940                       960
        *                   *                         *
ACG CAC GGC AAC TCG GCC ATG AAC CCC ATT GTC TAT GCC TTC CGC ATC
 T   H   G   N   S   A   M   N   P   I   V   Y   A   F   R   I>

980                       1000
                  *                          *              *
CAG AAG TTC CGC GTC ACC TTC CTT AAG ATT TGG AAT GAC CAT TTC CGC
 Q   K   F   R   V   T   F   L   K   I   W   N   D   H   F   R>

1020                1040
  *     *            *      *                  *
TGC CAG CCT GCA CCT CCC ATT GAC GAG GAT CTC CCA GAA GAG AGG CCT
 C   Q   P   A   P   P   I   D   E   D   L   P   E   E   R   P>
```

FIG. 1 IB

```
               1060                          1080                         1100
                 *              *              *              *              *
         GAT GAC TAG ACC CCG CCT TCC GCT CCC ACC AGC CCA CAT CCA GTG GGG
          D   D   *>

1120                         1140
                 *              *              *              *              *
         TCT CAG TCC AGT CCT CAC ATG CCC GCT GTC CCA GGG GTC TCC CTG AGC 1160                         1180                         1200
                 *              *              *              *              *
         CTG CCC CAG CTG GGC TGT TGG CTG GGG GCA TGG GGG AGG CTC TGA AGA 1220                         1240
                 *              *              *              *
         GAT ACC CAC AGA GTG TGG TCC CTC CAC TAG GAG TTA ACT ACC CTA CAC 1260                         1280
                 *              *              *              *              *
         CTC TGG GCC CTG CAG GAG GCC TGG GAG GGA AGG GTC CTA CGG AGG GAC

```
         10           20           30           40
          *            *            *            *
CAA TTT TCA GCT GTT CTT TGC TCA ATA ATA ACT TTT TTA TCA CCA AGA 50           60           70           80           90
     *            *            *            *            *
TAT CTC TCT AAG TTT TTG ACA TAT TCC TCA TTT GTT TTG ATA AAA GTT 100          110          120          130          140
       *            *            *            *            *
TTC TTA TTT TCT TAG AAA AAT AAG TTA CTA AAA GTC ATA TAT CAT TGT 150          160          170          180          190
         *            *            *            *            *
ATA TCT TCA AAA TAT TGC TTA AAA CTA GGA CTT GTA TTT AAA TGT TTT 200          210          220          230          240
       *            *            *            *            *
TTC TTC TTA AAG ACA ATT TGC AGG TGC CCT CAG GAA CCC TGA AGC TGG 250          260          270          280
            *            *            *            *
GCT GAG CCA TGA TGC TGC TGC CAG AAC CCC TGC AGA GGG CCT GGT TTC 290          300          310          320          330
  *            *            *            *            *
AGG AGA CTC AGA GTC CTC TGT GAA AAA GCC CTT GGA GAG CGC CCC AGC 340          350          360          370          380
      *            *            *            *            *
AGG GCT GCA CTT GGC TCC TGT GAG GAA GGG GCT CAG GGG TCT GGG CCC 390          400          410          420          430
      *            *            *            *            *
CTC CGC CTG GGC CGG GCT GGG AGC CAG GCG GGC GGC TGG GCT GCA GCA 440          450          460          470          480
        *            *            *            *            *
AAT GGA CCG TGA GCT GGC CCA GCC CGC GTC CGT GCT GAG CCT GCC TGT 490          500          510          520          530
            *            *            *            *            *
CGT CTG TGG CC ATG CCC ATC ATG GGC TCC TCG GTG TAC ATC ACG GTG GAG
              M   P   I   M   G   S   S   V   Y   I   T   V   E>

540          550          560          570
          *            *            *            *
CTG GCC ATT GCT GTG CTG GCC ATC CTG GGC AAT GTG CTG GTG TGC TGG
 L   A   I   A   V   L   A   I   L   G   N   V   L   V   C   W>

580          590          600          610          620
   *            *            *            *            *
GCC GTG TGG CTC AAC AGC AAC CTG CAG AAC GTC ACC AAC TAC TTT GTG
 A   V   W   L   N   S   N   L   Q   N   V   T   N   Y   F   V>
```

FIG. 12A

```
         630              640              650              660              670
          *                *                *                *                *
GTG TCA CTG GCG GCG GCC GAC ATC GCA GTG GGT GTG CTC GCC ATC CCC
 V   S   L   A   A   A   D   I   A   V   G   V   L   A   I   P>

680              690              700              710              720
          *                *                *                *                *
TTT GCC ATC ACC ATC AGC ACC GGG TTC TGC GCT GCC TGC CAC GGC TGC
 F   A   I   T   I   S   T   G   F   C   A   A   C   H   G   C>

730              740              750              760              770
          *                *                *                *                *
CTC TTC ATT GCC TGC TTC GTC CTG GTC CTC ACG CAG AGC TCC ATC TTC
 L   F   I   A   C   F   V   L   V   L   T   Q   S   S   I   F>

780              790              800              810
          *                *                *                *
AGT CTC CTG GCC ATC GCC ATT GAC CGC TAC ATT GCC ATC CGC ATC CCG
 S   L   L   A   I   A   I   D   R   Y   I   A   I   R   I   P>

820              830              840              850              860
 *                *                *                *                *
CTC CGG TAC AAT GGC TTG GTG ACC GGC ACG AGG GCT AAG GGC ATC ATT
 L   R   Y   N   G   L   V   T   G   T   R   A   K   G   I   I 870              880              890              900              910
          *                *                *                *                *
GCC ATC TGC TGG GTG CTG TCG TTT GCC ATC GGC CTG ACT CCC ATG CTA
 A   I   C   W   V   L   S   F   A   I   G   L   T   P   M   L>

920              930              940              950              960
          *                *                *                *                *
GGT TGG AAC AAC TGC GGT CAG CCA AAG GAG GGC AAG AAC CAC TCC CAG
 G   W   N   N   C   G   Q   P   K   E   G   K   N   H   S   Q>

970              980              990             1000             1010
          *                *                *                *                *
GGC TGC GGG GAG GGC CAA GTG GCC TGT CTC TTT GAG GAT GTG GTC CCC
 G   C   G   E   G   Q   V   A   C   L   F   E   D   V   V   P>

1020             1030             1040             1050
                *                *                *                *
ATG AAC TAC ATG GTG TAC TTC AAC TTC TTT GCC TGT GTG CTG GTG CCC
 M   N   Y   M   V   Y   F   N   F   F   A   C   V   L   V   P>

1060             1070             1080             1090             1100
 *                *                *                *                *
CTG CTG CTC ATG CTG GGT GTC TAT TTG CGG ATC TTC CTG GCG GCG CGA
 L   L   L   M   L   G   V   Y   L   R   I   F   L   A   A   R>

1110             1120             1130             1140             1150
          *                *                *                *                *
CGA CAG CTG AAG CAG ATG GAG AGC CAG CCT CTG CCG GGG GAG CGG GCA
 R   Q   L   K   Q   M   E   S   Q   P   L   P   G   E   R   A>
```

FIG. 12B

```
      1160          1170          1180          1190          1200
        *             *             *             *             *
CGG TCC ACA CTG CAG AAG GAG GTC CAT GCT GCC AAG TCA CTG GCC ATC
 R   S   T   L   Q   K   E   V   H   A   A   K   S   L   A   I>

1210          1220          1230          1240          1250
        *             *             *             *             *
ATT GTT GGG CTC TTT GCC CTC TGC TGG CTG CCC CTA CAC ATC ATC AAC
 I   V   G   L   F   A   L   C   W   L   P   L   H   I   I   N>

1260          1270          1280          1290
        *             *             *             *
TGC TTC ACT TTC TTC TGC CCC GAC TGC AGC CAC GCC CCT CTC TGG CTC
 C   F   T   F   F   C   P   D   C   S   H   A   P   L   W   L>

1300          1310          1320          1330          1340
  *             *             *             *             *
ATG TAC CTG GCC ATC GTC CTC TCC CAC ACC AAT TCG GTT GTG AAT CCC
 M   Y   L   A   I   V   L   S   H   T   N   S   V   V   N   P>

1350          1360          1370          1380          1390
        *             *             *             *             *
TTC ATC TAC GCC TAC CGT ATC CGC GAG TTC CGC CAG ACC TTC CGC AAG
 F   I   Y   A   Y   R   I   R   E   F   R   Q   T   F   R   K>

1400          1410          1420          1430          1440
        *             *             *             *             *
ATC ATT CGC AGC CAC GTC CTG AGG CAG CAA GAA CCT TTC AAG GCA GCT
 I   I   R   S   H   V   L   R   Q   Q   E   P   F   K   A   A>

1450          1460          1470          1480          1490
        *             *             *             *             *
GGC ACC AGT GCC CGG GTC TTG GCA GCT CAT GGC AGT GTC GGA GAG CAG
 G   T   S   A   R   V   L   A   A   H   G   S   V   G   E   Q>

1500          1510          1520          1530
        *             *             *             *
GTC AGC CTC CGT CTC AAC GGC CAC CCG CCA GAG GTG TGG GCC AAC GGC
 V   S   L   R   L   N   G   H   P   P   E   V   W   A   N   G>

1540          1550          1560          1570          1580
  *             *             *             *             *
AGT GCT CCC CAC CCT GAG CGG AGG CCC AAT GGC TAC GCC CTG GGG CTG
 S   A   P   H   P   E   R   R   P   N   G   Y   A   L   G   L>

1590          1600          1610          1620          1630
        *             *             *             *             *
GTG AGT GGA GGG AGT GCC CAA GAG TCC CAG GGG AAC ACG GGC CTC CCA
 V   S   G   G   S   A   Q   E   S   Q   G   N   T   G   L   P>

1640          1650          1660          1670          1680
        *             *             *             *             *
GAC GTG GAG CTC CTT AGC CAT GAG CTC AAG AGA GTG TGC CCA GAG CCC
 D   V   E   L   L   S   H   E   L   K   R   V   C   P   E   P>
```

FIG. 12C

```
        1690            1700            1710            1720            1730
         *               *               *               *               *
CCT GGC CTA GAT GAC CCC CTG GCC CAG GAT GGA GCA GGA GTG TCC TGA T
 P   G   L   D   D   P   L   A   Q   D   G   A   G   V   S   *>

1740            1750            1760            1770
         *               *               *               *
GAT TCA TGG AGT TTG CCC CTT CCT AAG GGA AGG AGA TCT TTA TCT TTC 1780            1790            1800            1810            1820
  *               *               *               *               *
TGG TTG GCT TGA CCA GTC ACG TTG GGA GAA GAG AGA GAG TGC CAG GAG 1830            1840            1850            1860            1870
     *               *               *               *               *
ACC CTG AGG GCA GCC GGT TCC TAC TTT GGA CTG AGA GAA GGG AGC CCC 1880            1890            1900            1910            1920
         *               *               *               *               *
AGG CTG GAG CAG CAT GAG GCC CAG CAA GAA GGG CTT GGG TTC TGA GGA 1930            1940            1950            1960            1970
         *               *               *               *               *
AGC AGA TGT TTC ATG CTG TGA GGC CTT GCA CCA GGT GGG GGC CAC AGC 1980            1990            2000            2010
             *               *               *               *
ACC AGC AGC ATC TTT GCT GGG CAG GGC CCA GCC CTC CAC TGC AGA GCC 2020            2030            2040            2050            2060
  *               *               *               *               *
ATC TGG AAG CAC CAC CTT GTC TCC ACA GAG CAG CTT GGG CAC AGC AGA 2070            2080            2090            2100            2110
     *               *               *               *               *
CTG GCC TGG CCC TGA GAC TGG GGA GTG GCT CCA ACA GCC TCC TGC CAC 2120            2130            2140            2150            2160
         *               *               *               *               *
CCA CAC ACC ACT CTC CCT AGA CTC TCC TAG GGT TCA GGA GCT GCT GGG 2170            2180            2190            2200            2210
         *               *               *               *               *
CCC AGA GGT GAC ATT TGA CTT TTT TTC CAG GAA AAA TGT AAG TGT GAG 2220            2230            2240            2250
             *               *               *               *
GAA ACC CTT TTT ATT TTA TTA CCT TTC ACT CTC TGG CTG CTG GGT CTG 2260            2270            2280            2290            2300
  *               *               *               *               *
CCG TCG GTC CTG CTG CTA ACC TGG CAC CAG AGC CTC TGC CCG GGG AGC
```

FIG. 12D

```
     2310            2320            2330            2340            2350
       *               *               *               *               *
 CTC AGG CAG TCC TCT CCT GCT GTC ACA GCT GCC ATC CAC TTC TCA GTC 2360            2370            2380            2390            2400
       *               *               *               *               *
 CCA GGG CCA TCT CTT GGA GTG ACA AAG CTG GGA TCA AGG ACA GGG AGT 2410            2420            2430            2440            2450
       *               *               *               *               *
 TGT AAC AGA GCA GTG CCA GAG CAT GGG CCC AGG TCC CAG GGG AGA GGT 2460            2470            2480            2490
       *               *               *               *
 TGG GGC TGG CAG GCC ACT GGC ATG TGC TGA GTA GCG CAG AGC TAC CCA 2500            2510            2520            2530            2540
  *               *               *               *               *
 GTG AGA GGC CTT GTC TAA CTG CCT TTC CTT CTA AAG GGA ATG TTT TTT 2550            2560            2570
  *               *               *
 TCT GAG ATA AAA TAA AAA CGA GCC ACA G
```

FIG. 12E

```
          10        20        30        40        50        60
           *         *         *         *         *         *
-GGACCTCTGGGAAGACGTCTGGCGAGAGCTAGGCCCACTGGCCCTACAGACGGATCTTGC 70        80        90       100       110
           *         *         *         *         *
TGGCTCACCTGTCCCTGTGGAGGTTCCCCTGGGAAGGCAAG ATG CCC AAC AAC
                                          Met Pro Asn Asn>

120           130           140           150
          *             *             *             *
AGC ACT GCT CTG TCA TTG GCC AAT GTT ACC TAC ATC ACC ATG GAA
Ser Thr Ala Leu Ser Leu Ala Asn Val Thr Tyr Ile Thr Met Glu>

160           170           180           190           200
 *             *             *             *             *
ATT TTC ATT GGA CTC TGC GCC ATA GTG GGC AAC GTG CTG GTC ATC
Ile Phe Ile Gly Leu Cys Ala Ile Val Gly Asn Val Leu Val Ile>

210           220           230           240
          *             *             *             *
TGC GTG GTC AAG CTG AAC CCC AGC CTG CAG ACC ACC ACC TTC TAT
Cys Val Val Lys Leu Asn Pro Ser Leu Gln Thr Thr Thr Phe Tyr>

250           260           270           280           290
 *             *             *             *             *
TTC ATT GTC TCT CTA GCC CTG GCT GAC ATT GCT GTT GGG GTG CTG
Phe Ile Val Ser Leu Ala Leu Ala Asp Ile Ala Val Gly Val Leu>

300           310           320           330
          *             *             *             *
GTC ATG CCT TTG GCC ATT GTT GTC AGC CTG GGC ATC ACA ATC CAC
Val Met Pro Leu Ala Ile Val Val Ser Leu Gly Ile Thr Ile His>

340           350           360           370           380
 *             *             *             *             *
TTC TAC AGC TGC CTT TTT ATG ACT TGC CTA CTG CTT ATC TTT ACC
Phe Tyr Ser Cys Leu Phe Met Thr Cys Leu Leu Leu Ile Phe Thr>

390           400           410           420
          *             *             *             *
CAC GCC TCC ATC ATG TCC TTG CTG GCC ATC GCT GTG GAC CGA TAC
His Ala Ser Ile Met Ser Leu Leu Ala Ile Ala Val Asp Arg Tyr>

430           440           450           460           470
 *             *             *             *             *
TTG CGG GTC AAG CTT ACC GTC AGA TAC AAG AGG GTC ACC ACT CAC
Leu Arg Val Lys Leu Thr Val Arg Tyr Lys Arg Val Thr Thr His>

480           490           500           510
          *             *             *             *
AGA AGA ATA TGG CTG GCC CTG GGC CTT TGC TGG CTG GTG TCA TTC
Arg Arg Ile Trp Leu Ala Leu Gly Leu Cys Trp Leu Val Ser Phe>
```

FIG. 13A

```
       520           530           540           550           560
        *             *             *             *             *
CTG GTG GGA TTG ACC CCC ATG TTT GGC TGG AAC ATG AAA CTG ACC
Leu Val Gly Leu Thr Pro Met Phe Gly Trp Asn Met Lys Leu Thr>

570           580           590           600
              *             *             *             *
TCA GAG TAC CAC AGA AAT GTC ACC TTC CTT TCA TGC CAA TTT GTT
Ser Glu Tyr His Arg Asn Val Thr Phe Leu Ser Cys Gln Phe Val>

610           620           630           640           650
  *             *             *             *             *
TCC GTC ATG AGA ATG GAC TAC ATG GTA TAC TTC AGC TTC CTC ACC
Ser Val Met Arg Met Asp Tyr Met Val Tyr Phe Ser Phe Leu Thr>

660           670           680           690
              *             *             *             *
TGG ATT TTC ATC CCC CTG GTT GTC ATG TGC GCC ATC TAT CTT GAC
Trp Ile Phe Ile Pro Leu Val Val Met Cys Ala Ile Tyr Leu Asp>

700           710           720           730           740
  *             *             *             *             *
ATC TTT TAC ATC ATT CGG AAC AAA CTC AGT CTG AAC TTA TCT AAC
Ile Phe Tyr Ile Ile Arg Asn Lys Leu Ser Leu Asn Leu Ser Asn>

750           760           770           780
              *             *             *             *
TCC AAA GAG ACA GGT GCA TTT TAT GGA CGG GAG TTC AAG ACG GCT
Ser Lys Glu Thr Gly Ala Phe Tyr Gly Arg Glu Phe Lys Thr Ala>

790           800           810           820           830
  *             *             *             *             *
AAG TCC TTG TTT CTG GTT CTT TTC TTG TTT GCT CTG TCA TGG CTG
Lys Ser Leu Phe Leu Val Leu Phe Leu Phe Ala Leu Ser Trp Leu>

840           850           860           870
              *             *             *             *
CCT TTA TCT ATC ATC AAC TGC ATC ATC TAC TTT AAT GGT GAG GTA
Pro Leu Ser Ile Ile Asn Cys Ile Ile Tyr Phe Asn Gly Glu Val>

880           890           900           910           920
  *             *             *             *             *
CCA CAG CTT GTG CTG TAC ATG GGC ATC CTG CTG TCC CAT GCC AAC
Pro Gln Leu Val Leu Tyr Met Gly Ile Leu Leu Ser His Ala Asn>

930           940           950           960
              *             *             *             *
TCC ATG ATG AAC CCT ATC GTC TAT GCC TAT AAA ATA AAG AAG TTC
Ser Met Met Asn Pro Ile Val Tyr Ala Tyr Lys Ile Lys Lys Phe>

970           980           990           1000          1010
  *             *             *             *             *
AAG GAA ACC TAC CTT TTG ATC CTC AAA GCC TGT GTG GTC TGC CAT
Lys Glu Thr Tyr Leu Leu Ile Leu Lys Ala Cys Val Val Cys His>
```

FIG. 13B

```
         1020           1030           1040           1050
           *              *              *              *
    CCC TCT GAT TCT TTG GAC ACA AGC ATT GAG AAG AAT TCT GAG TAG
    Pro Ser Asp Ser Leu Asp Thr Ser Ile Glu Lys Asn Ser Glu ***>

1060      1070      1080      1090      1100      1110
    *         *         *         *         *         *
    TTATCCATCAGAGATGACTCTGTCTCATTGACCTTCAGATTCCCCATCAACAAACACTTG 1120      1130      1140      1150      1160      1170
    *         *         *         *         *         *
    AGGGCCTGTATGCCTGGGCCAAGGGATTTTTACATCCTTGATTACTTCCACTGAGGTGGG 1180      1190      1200      1210      1220      1230
    *         *         *         *         *         *
    AGCATCTCCAGTGCTCCCCAATTATATCTCCCCCACTCCACTACTCTCTTCCTCCACTTC 1240      1250      1260      1270      1280      1290
    *         *         *         *         *         *
    ATTTTTCCTTTGTCCTTTCTCTCTAATTCAGTGTTTTGGAGGCCTGACTTGGGGACAACG 1300      1310      1320      1330      1340      1350
    *         *         *         *         *         *
    TATTATTGATATTATTGTCTGTTTTCCTTCTTCCCAATAGAAGAATAAGTCATGGAGCCT 1360      1370
    *         *
    GAAGGGTGCCTAGTTGAC
```

FIG. 13C

METHODS AND COMPOSITIONS FOR REDUCING ISCHEMIC INJURY OF THE HEART BY ADMINISTERING ADENOSINE RECEPTOR AGONISTS AND ANTAGONISTS

This application claims priority under 35 U.S.C. §119(e) to U.S. Provisional Applications 60/046,030 and 60/061,716 filed May 9, 1997 and Oct. 10, 1997, respectively.

Pursuant to 35 U.S.C. §202(c) it is acknowledged that the U.S. Government has certain rights in the invention described herein, which was made in part with funds from the National Institutes of Health, Grant Number HL48225.

FIELD OF THE INVENTION

The present invention relates to therapeutic methods for protecting the heart from ischemic injury. More specifically, the methods of the invention involve administering agonists and antagonists or binary conjugates thereof which selectively activate or inhibit adenosine receptors simultaneously thereby enhancing the protective effects of preconditioning and rendering the myocardium more resistant to ischemia.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Adenosine is released in large amounts during myocardial ischemia and can mediate potentially A important protective functions in the cardiovascular system (1,4,5,7,9,14, 17,18, 19,25). Previous studies have shown that adenosine receptor agonists can precondition the heart when given before the onset of ischemia (4,5,9,14,17,18) and can cause reduction in infarct size or improvement in left ventricular function when given during reperfusion (1,19) or during both low-flow ischemia and reperfusion in isolated perfused heart (6,21,22). While activation of adenosine A1 and A3 receptors has been shown to mimic the cardioprotective effect of preconditioning (3,10,23,24), their roles in mediating the protective effect of adenosine administered during ischemia have not yet been fully elucidated. Further, the cardioprotective effect of exogenous adenosine infused during ischemia in the intact heart may be exerted at the level of coronary vasculature, circulating neutrophils, or cardiac myocytes.

Our previous studies have characterized a cardiac myocyte model of injury, which is induced by exposure of myocytes to prolonged hypoxia in glucose-free media (16, 23). Use of this model has facilitated the identification of compounds that enhance the protective effects of preconditioning and also increase myocardial resistance to ischemia.

SUMMARY OF THE INVENTION

The present invention provides methods for preventing or reducing ischemic damage of the heart. In conducting research leading up to this invention, it was discovered that simultaneous activation of A3 and A1 receptors enhances the protective effects of preconditioning and increases myocardial resistance to ischemia. The concept underlying the present invention is the use of specific agonists which simultaneously activate these two adenosine receptors. Concomitant activation of the two receptors is believed to produce a synergistic effect enhancing the cardioprotective effects of preconditioning and increasing myocardial resistance to ischemia.

According to a preferred embodiment, the invention involves administration of specific A1/A3 agonists, such as $N^6$-(2-trifluoromethyl)(carbamoyl)adenosine-5'uronamide or $N^6$-(3-iodophenyl)(carbamoyl)adenosine-5'uronamide during ischemic attacks, or at risk for ischemic damage. The agonists of the invention may be delivered prior to a surgical procedure. They may also be administered to a patient to prevent or reduce the severity of ischemic damage during surgery. Additionally, the A3/A1 agonists may be administered following surgical procedures to reduce the risk of post-surgical ischemic complications. Finally, the A3/A1 agonists may be administered to patients with angina or to patients during a myocardial infarction. The angina may be chronic and stable, unstable, or post-myocardial infarction angina.

In yet another embodiment of the invention, a series of water-soluble MRS compounds are contemplated to be within the scope of the present invention. These compounds selectively activate the A3 receptor. Because the compounds of the invention do not cross the blood-brain barrier, the deleterious effects associated with A3 receptor activation in the brain are avoided. The MRS compounds will be used in conjunction with the A1 agonists of the invention to prevent or reduce ischemic damage to the heart.

Another preferred embodiment of the invention comprises novel binary conjugates which bind two adenosine receptors simultaneously. Exemplary binary conjugates of the invention contain moieties that act as agonists at both of the A1 and A3 adenosine receptors, such as MRS 1543. A second exemplary conjugate, MRS 1528, acts simultaneously as an agonist at the A3 receptor and as an antagonist at the A2a receptor. Methods are disclosed herein for the administration of these binary conjugates to protect the heart against ischemic damage.

Methods of simultaneous administration of the A3 and A1 agonists or the binary A3 agonist/A2a antagonist or the binary A3 agonist/A1 agonist of the invention include direct perfusion of the organ during surgery and intravenous administration. Additionally, the agonists and antagonists of the invention may be administered to patients in tablet form in an amount effective to prevent or reduce ischemic damage to the heart.

In yet a further aspect of the invention, recombinant myocytes are provided which may be used to advantage in assessing the activity of agents that may possess cardioprotective activity. Cardiac myocytes may be transfected with any of the adenosine receptor encoding cDNAs and used to screen for novel therapeutic agents.

BRIEF DESCRIPTION OF THE DRAWINGS

FIG. 3A shows the amount of creatine kinase released as a function of increasing concentrations of MRS 584 in the presence (diamonds) or absence (open squares) of the A1 receptor antagonist DPCPX. FIG. 3B shows the amount of creatine kinase released as a function of increasing concentrations of MRS 537 in the presence (diamonds) or absence (open squares) of the A1 receptor antagonist DPCPX. FIG. 3C shows the amount of creatine kinase released as a function of increasing concentrations of MRS 479 in the presence (diamonds) or absence (open squares) of the A1 receptor antagonist DPCPX. FIG. 3D shows the amount of creatine kinase released as a function of increasing concentrations of MRS 1340 in the presence (diamonds) or absence (open squares) of the A1 receptor antagonist DPCPX. FIG. 3E shows that both MRS584 and MRS537 can exert the cardioprotective effect of preconditioning via the human adenosine A3 receptor. Data represent means +SE of three experiments. FIG. 3F shows that Cl-IB-MECA reduces the percentage of myocytes killed during ischemia.

FIG. 4A shows that the preconditioning effect is synergistically enhanced when adenosine A1 and A3 receptors are activated simultaneously, as opposed to activation of a single receptor. The percentage of myocytes killed is also significantly reduced in the simultaneous presence of A1 and A3 agonists during prolonged ischemia. See FIG. 4B. Data represent means ±SE of four experiments.

FIG. 5A shows that MRS646 and MRS1364 can pharmacologically precondition the cardiac myocyte. The extent of myocyte injury was quantitated as percentage of myocytes killed. The data show that when either MRS646 or MRS1364 was present during the injury-producing ischemia, both compounds protect against injury. See FIG. 5B. FIG. 5C shows that MRS 1364 was able to pharmacologically precondition the cardiac myocytes transfected with the human adenosine A3 receptor. Data represent the means ±S.E. of three experiments. FIG. 5D shows that MRS 646 was able to pharmacologically precondition the cardiac myocytes transfected with the human adenosine A3 receptor. Data represent the means ±S.E. of three experiments.

FIG. 6A shows that the protective effect of MRS1543 was only partially attenuated by DPCPX or by MRS1191. Ventricular myocytes were exposed to the indicated concentrations of MRS1543 in the presence or the absence of excess DPCPX (1 μM) or excess MRS1191 (1 μM). The ventricular myocytes were also exposed to the indicated concentrations of MRS1543 in the presence or the absence of excess DPCPX (1 μM) plus excess MRS1191 (1 μM). See FIG. 6B. The combined presence of both DPCPX and MRS1191 completely abolished the protective effect of MRS1543. The protective effect of MRS1543 in chick cells transfected with the human adenosine A3 receptor is shown in FIG. 6C. Data represent means ±SE of three experiments.

FIG. 7A shows that an $A_{2a}$ antagonist enhances the ability of an A3/A1 agonist, MRS 580, to cause preconditioning. FIG. 7B shows that an $A_{2a}$ antagonist enhances the protective effect of MRS 580 during prolonged ischemia.

FIG. 8A shows that the ability of MRS1528 to cause preconditioning is not affected by the presence of 8-(3-chlorostyryl)caffeine, (CSC). Myocytes were exposed to the indicated concentrations of MRS1528 in the presence or the absence of CSC (1 μM). Myocytes were also exposed to the indicated concentrations of MRS1528 in the presence or the absence of CGS21680 (0.3 μM). See FIG. 8B. FIG. 8C shows the results obtained when myocytes were exposed to MRS1525 in the presence or the absence of CSC. FIG. 8D shows the results obtained when myocytes were exposed to the indicated concentrations of MRS1525 in the presence or the absence of CGS21680. The preconditioning effect of MRS1528 in cells transfected with the human adenosine A3 receptor is shown in FIG. 8E. Data represent the means ±SE of three experiments.

FIGS. 10A–10C depict diagrams for synthesizing certain compounds of the invention. FIGS. 10A and 10B show a synthetic scheme for synthesizing a derivative of an A1 selective agonist for coupling to an amine derived A3 agonist. FIG. 10C is a schematic diagram showing the synthesis of binary conjugates with extended linkers.

FIGS. 11A and 11C show the nucleotide sequence of the cDNA encoding the adenosine A1 receptor.

FIGS. 12A–12E show the nucleotide sequence of the cDNA encoding the adenosine A2a receptor.

FIGS. 13A–13C show the nucleotide sequence of the cDNA encoding the adenosine A3 receptor.

DETAILED DESCRIPTION OF THE INVENTION

Figure 1A:
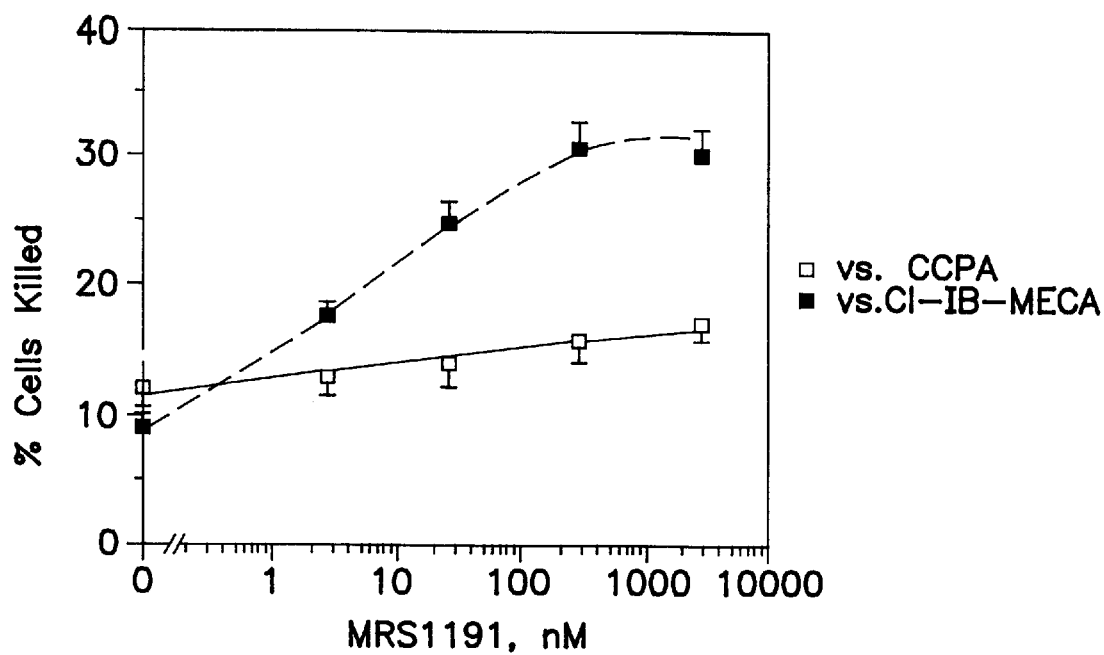
FIGS. 1A and 1B are graphs showing the effects of adenosine A3 receptor antagonists on the 2-chloro-$N^6$-cyclopentyl-adenosine (CCPA) and 2-chloro-$N^6$-(3-iodobenzyl)adenosine-5'-N-methyluronamide (Cl-IB-MECA)-induced cardioprotective effect. Cultured ventricular myocytes were prepared and the extent of hypoxia-induced myocyte injury determined as described hereinbelow. The A3 antagonist, 3-ethyl-5-benzyl-2-methyl-6-phenyl-4-phenylethynyl-1,4-(1)-dihydropyridine-3,5-dicarboxylate (MRS 1191) was present at the indicated concentrations individually, with CCPA (10 nM), or with Cl-IB-MECA (10 nM) during the ninety-minute hypoxia. The percentage of myocytes killed, FIG. 1A and the amount of CK released, FIG., 1B, were determined following the prolonged hypoxia. Data represent the mean ±SE of three experiments.

The cardioprotective roles of adenosine A1 and A3 receptors were investigated in a cardiac myocyte model of injury. The adenosine A3 receptor is a novel cardiac receptor capable of mediating potentially important cardioprotective functions. Prolonged hypoxia with glucose deprivation was used to simulate ischemia and to induce injury in cardiac ventricular myocytes cultured from chick embryos 14 days in ovo. When present during the prolonged hypoxia, the adenosine A3 agonists N6-(3-iodobenzyl)adenosine-5'-N-methyluronamide (IB-MECA) and Cl-IB-MECA caused a dose-dependent reduction in the extent of hypoxia-induced injury, as manifested by a decrease in the amount of creatine kinase released and the percentage of myocytes killed. The adenosine A1 agonists CCPA and N6-cyclohexyladenosine (CHA) were also able to cause a decrease in the extent of myocyte injury. The A1 receptor-selective antagonist DPCPX blocked the cardioprotective effect of the A1 but not of the A3 agonists. Conversely, selective A3 antagonists MRS1191 and 3,5-Diethyl 2-methyl-6-phenyl-4-[2-phenyl-(E)-vinyl]-1,4-(1)-dihydropyridine-3,5-dicarbo xylate (MRS 1097) blocked the protection induced by Cl-IB-MECA but had minimal effect on that caused by CCPA. Thus, the cardioprotective effects of A1 and A3 agonists were mediated by their respective receptors. The study identifies the cardioprotective function of the cardiac A3 receptor and provides conclusive evidence that simultaneous activation of both A1 and A3 receptors during hypoxia can attenuate myocyte injury. This finding is in contrast to that set forth by Downey et al. in U.S. Pat. No. 5,573,772 wherein administration of antagonists to the A1 receptor in conjuction with agonists at the A3 receptor was reported to enhance cardioprotective effects during ischemia. Administration of an adenosine A1 receptor antagonist is not required for practicing the present invention.

The present invention also includes administration of binary reagents that selectively activate the A1 and A3 adenosine receptors simultaneously. Concomitant activation of the two receptors is believed to act synergistically to enhance the cardioprotective effects of preconditioning and to increase myocardial resistance to ischemia.

Several new MRS compounds are disclosed which selectively activate the A3 adenosine receptor. See FIGS. 3A–3F. These compounds are also contemplated for use in the methods of the present invention.

In accordance with another aspect of the invention, a binary conjugate has been developed, which binds both the A3 and A2a receptors simultaneously and elicits the desired result, i.e., activation of the A3 receptor and inhibition of the A2a receptor.

A second binary conjugate, has also been synthesized in accordance with this invention which simultaneously binds and activates both of the A1 and the A3 receptors. These binary compounds may also be used to advantage in practicing the methods of the present invention. The following definitions are provided to facilitate understanding of the present invention.

Preconditioning ischemia—A brief ischemia which does not cause any cardiac damage, but is able to protect the heart against damage during a subsequent prolonged ischemia. The effect of preconditioning ischemia is mediated by adenosine, which is released during the ischemia. Preconditioning may be induced by brief exposure to anoxic conditions for example.

Adenosine receptors—A1, A3 and A2a receptors are present on the myocardium (cardiac muscle cells). While activation of the A1 and A3 receptors is cardioprotective, activation of the A2a receptors is deleterious and causes damage to the cardiac muscle cells.

Stable angina—Condition observed in certain cardiac patients having a chronic risk for mycardial ischemia because of the chronic potential for an imbalance between the supply of oxygenated blood and the demand for it. Typically, such imbalance occurs during certain stresses, such as exercise, emotional stress or stress associated with a surgical procedure.

Unstable angina—Condition observed in cardiac patients having frequent imbalance between the supply of and the demand for oxygenated blood.

Post-myocardial infarction angina—Condition observed in patients who have recurrent ischemia following a heart attack.

Preconditioning stimuli—Any drug, agent or treatment which induces preconditioning, such as brief ischemia, or A1 or A3 receptor agonists.

Myocardial responsiveness—The myocardium can be treated so as to enhance the effectiveness and protective effects of preconditioning. This enhancement leads to a reduction in ischemic damage.

Representative examples of compounds used for practicing the present invention are as follows
A1 agonists—CCPA, and compounds listed in Table I.
A1 antagonists—DPCPX
A3 agonists—IB-MECA, Cl-IB-MECA, MRS 584, MRS 537, MRS 479, MRS 1340, DBXMR, NNC21-0238, NN53-0055
A3 antagonists—MRS 1191
A2a agonists—CGS21680
A2a antagonists—CSC
Binary A3/A1 agonists—MRS 1543
Binary A3 agonist/A2a antagonists—MRS 1528
Mixed A3/A1 agonists—compounds listed in Table II, including MRS 580 and MRS 1364

The present invention demonstrates that activation of adenosine receptors during prolonged hypoxia can attenuate the hypoxia-induced myocyte injury. Specifically, activation of A1 and A3 receptors has been shown to mediate adenosine-induced cardiac myocyte protection. Additionally, the concomittant activation of the A3 receptor coupled with inhibition of A2a receptor activation by a selective binary conjugate has also been shown to attenuate hypoxia-induced myocyte injury. The following methods facilitate the practice of the present invention.

Preparation of Cultured Ventricular Cells

Ventricular cells were cultured from chick embryos 14 days in ovo as previously described (16, 23). Cells were cultivated in a humidified 5% $CO_2$-95% air mixture at 37° C. All experiments were performed on day 3 in culture, at which time cells exhibited rhythmic spontaneous contraction. The medium was changed to a HEPES-buffered medium containing (mM) 139 NaCl, 4.7 KCl, 0.5 $MgCl_2$, 0.9 $CaCl_2$, 5 HEPES (N-2-hydroxyethylpiperazine-N'-2-ethanesulfonic acid) and 2% fetal bovine serum, pH 7.4, 37° C. before exposing the myocytes to the various conditions at 37° C. Control myocytes were maintained in the HEPES-buffered media under room air. Ninety-minute exposure of the myocytes to hypoxia with glucose deprivation was used to induce cell injury. Hypoxia was produced by placing the cells in a hypoxic incubator (NuAire) where $O_2$ was replaced by $N_2$ as previously described (16,23). Effects of adenosine receptor agonists and antagonists on the extent of myocyte injury were determined by exposure of the prepared cells to these agents during the prolonged hypoxia.

Determination of Cell Injury

Determination of myocyte injury was made at the end of the ninety-minute hypoxia, at which time myocytes were taken out of the hypoxic incubator and re-exposed to room air (normal % $O_2$). Aliquots of the media were then obtained for creatine kinase (CK) activity measurement, which is followed by quantitation of the number of viable cells. Measurement of basal level of cell injury was made after parallel incubation of control cells under normal % $O_2$. The extent of hypoxia-induced injury to the ventricular cell was quantitatively determined by the percentages of cells killed and by the amount of CK released into the media according to a previously described method (16, 23). Prior studies demonstrated that the cell viability assay distinguished the hypoxia-damaged from the control normoxia-exposed cells. In brief, the media were replaced with a trypsin-EDTA buffer to detach the cells, which was then followed by sedimentation of the viable myocytes. Parallel changes in % cells killed and CK released (16, 23) further validated this assay for % cells killed. The amount of CK was measured as enzyme activity (unit/mg), and increases in CK activity above the control level were determined. The percentage of cells killed was calculated as the number of cells obtained from the control group (representing cells not subjected to any hypoxia or drug treatment) minus the number of cells from the treatment group divided by number of cells in control group multiplied by 100%.

Synthesis of Adenosine A1 and A3 Receptor-selective Agents $N^6$-(3-iodobenzyl)adenosine-5'-N-methyluronamide (IB-MECA), 2-chloro-$N^6$-(3-iodobenzyl)adenosine-5'-N-methyluronamide (Cl-IB-MECA), and adenosine amine congener (ADAC) were synthesized as previously described (8,11,13). 3,5-Diethyl 2-methyl-6-phenyl-4-[2-phenyl-(E)-vinyl]-1,4-(1)-dihydropyridine-3,5-dicarboxylate (MRS 1097) and 3-ethyl 5-benzyl-2-methyl-6-phenyl-4-phenylethynyl-1,4-(1)-dihydropyridine-3,5-dicarboxylate (MRS 1191) were synthesized as previously described (12).

Adenosine Analogs 8-cyclopentyl-1,3-dipropylxanthine (DPCPX) and 2-chloro-$N^6$-cyclopentyladenosine (CCPA), $N^6$-cyclohexyladenosine (CHA) were from Research Biochemicals International (Natick, Mass.). Embryonic chick eggs were from Spafas Inc. (Storrs, Con.).

Transfection of chick atrial myocytes with the human A3 receptor—Atrial cells were cultured from chick embryos 14 days in ovo and transiently transfected with pcDNA3 (empty vector) or with pcDNA3/hA3R (full length cDNA encoding human adenosine A3 receptor subcloned in pcDNA3) using the calcium phosphate precipitation method. Forty-eight hours after transfection, the cells were exposed to the compounds of the invention and the percentage of myocytes killed during simulated ischemia was determined.

The following examples are provided to illustrate certain embodiments of the invention. They are not intended to limit the invention in any way.

EXAMPLE I

ACTIVATION OF A1 OR A3 ADENOSINE RECEPTORS REDUCES ISCHEMIC INJURY TO THE HEART

A. Exogenous Adenosine Causes a Decrease in the Extent of Cardiac Myocyte Injury During the Prolonged Hypoxia Prolonged exposure to hypoxia in glucose-free media induced significant cardiac myocyte injury with large increase in the release of creatine kinase (28.5±1.5 unit/mg, n=4, ±SE) and in the % cells killed (30±2%, n=4). Adenosine (10 μM), when added to the media during the ninety-minute hypoxia, caused a decrease in the amount of CK released (CK released in unit/mg=14.9±3, n=3) and in the % cells killed (% cells killed=12±2%, n=4). This effect of exogenous adenosine was blocked by the nonselective adenosine receptor antagonist 8-sulfophenyl-theophylline (8-SPT, at 100 μM) (in the presence of adenosine and 8-SPT: CK released in unit/mg=31±5 and % cells killed=28±3%, n=5). The presence of 8-SPT during the hypoxia had no effect on the level of myocyte injury (CK released=29.6+1.2 unit/mg; % cells killed=31.6±1.5%, n=3). These data suggest that activation of adenosine receptors during the prolonged hypoxia can protect the myocyte against injury. Since adenosine can activate both the cardiac A1 and A3 receptors and since 8-SPT, at 100 μM, can block both receptors (23), the data are consistent with the hypothesis that either receptor or both receptor subtypes can mediate the cardioprotective function of adenosine. This hypothesis was further explored using selective agonists and antagonists. See FIGS. 1, 2 and 3.

Figure 1B:
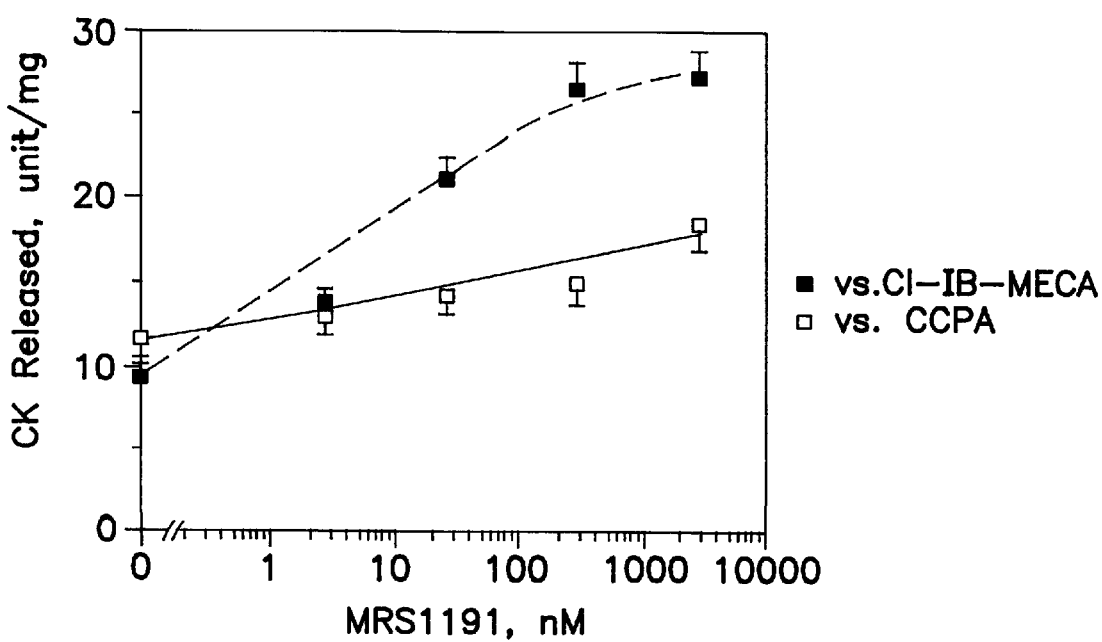

B. Adenosine A3 Agonists Mediate Cardioprotective Effects During Prolonged Hypoxia In order to examine whether activation of adenosine A3 receptors is capable of attenuating myocyte injury during the prolonged hypoxia, agonists selective at the A3 receptor were used. Prior study has demonstrated that both IB-MECA and Cl-IB-MECA are highly selective at the chick cardiac A3 receptor (23). Either A3 agonist, when present during the prolonged hypoxia, was capable of protecting the cardiac myocytes against hypoxia-induced injury (FIG. 1). The cardioprotective effect of A3 agonists was quantitated as a decrease in the amount of CK released and the percentage of myocytes killed (statistically significant at 1 and 10 nM of Cl-IB-MECA, ANOVA and t test, p<0.01).

The presence of the A1 receptor-selective antagonist DPCPX had no effect on the ability of IB-MECA or Cl-IB-MECA to mediate their cardioprotective effects; the A3 agonist-induced decreases in % cells killed and CK released were similar in the presence and absence of 1 μM of DPCPX (not shown). These data indicate that the cardioprotective effect of the A3 agonists was not due to activation of the cardiac A1 receptor.

To determine whether the A3 agonist-induced cardioprotection is mediated by the A3 receptor, antagonists selective at the A3 receptor were employed. FIG. 1 demonstrates that the A3 receptor-selective antagonist MRS 1191 blocked the Cl-IB-MECA-induced cardioprotection. The levels of CK released and of percentage of cells killed were significantly higher in myocytes exposed to Cl-IB-MECA and 30 nM, 300 nM or 3 μM of MRS 1191 (ANOVA and t test, p<0.01). Another A3 receptor antagonist, MRS1097, was also able to block the cardioprotective effect of Cl-IB-MECA (not shown). These data provide conclusive evidence that activation of the A3 receptor can produce a potent cardioprotective effect when administered during the prolonged hypoxia.

Figure 2:
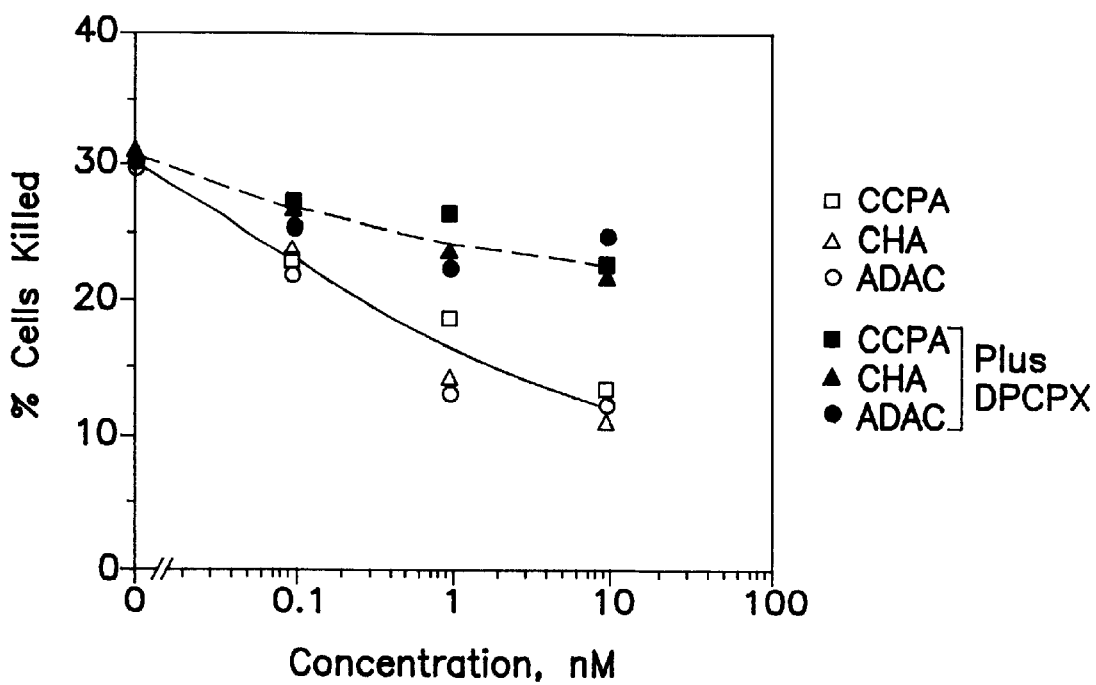
FIG. 2 is a graph showing effects of adenosine A1 agonists, 2-chloro-N⁶-cyclopentyladenosine (CCPA), N⁶-cyclohexyladenosine (CHA), and adenosine amine congener (ADAC) on cardiac myocyte injury in the presence or absence of excess 8-cyclopentyl-1,3-dipropylxanthine (DPCPX), an A1 antagonist. (open squares, CCPA; open triangles, CHA, open circles, ADAC; filled squares CCPA+ DPCPX; filled triangles, CHA+DPCPX; filled circles, ADAC+DPCPX)

C. Adenosine A1 Receptor Activation Reduces Cardiac Myocyte Injury During Prolonged Ischemia Since the A1 receptor is also present on the cardiac myocyte, an investigation was undertaken to determine whether activation of the A1 receptor can confer a cardioprotective effect during the prolonged hypoxia. Prior study showed that CCPA, a known A1 agonist, is highly selective at the A1 receptor on these cardiac myocytes (23). Cultured ventricular myocytes were prepared and the extent of hypoxia-mediated myocyte injury determined. The various adenosine A1 receptor agonists were added to the media at the indicated concentrations in the absence or the presence of the A1 receptor antagonist DPCPX during the prolonged hypoxia. The percentage of cells killed was determined following the hypoxic exposure and removal of the A1 receptor agonists and antagonist. The data represent the mean of four experiments. At 1 and 10 nM of the A1 agonists, the percentages of myocytes killed were significantly lower than those obtained in the presence of either of the two A1 agonist concentrations and DPCPX (1 μM) (ANOVA and t test, P<0.01). Thus, CCPA caused a dose-dependent reduction in the percentage of myocytes killed as shown in FIG. 2 and in the amount of CK released (not shown) (ANOVA and t test, p<0.01). Two other A1 receptor-selective agonists, ADAC and CHA, were also able to protect the myocytes when present during the prolonged hypoxia. The cardioprotection stimulated by CCPA, CHA and ADAC was blocked by the A1 antagonist DPCPX. On the other hand, neither MRS 1191 nor MRS 1097 was able to block the CCPA-induced cardioprotection as shown in FIG. 1, providing definitive evidence that the A1 agonist effect is mediated by the A1 receptor.

Although the number of viable cells was determined quickly following re-exposure of cardiac myocytes to normal % $O_2$ (reoxygenation), the A1 or the A3 agonist was nevertheless present briefly prior to replacement with the trypsin-EDTA buffer for cell viability assay. Thus, it is possible that the decrease in myocyte injury is due to the protection against a reoxygenation injury. To study this possibility, CCPA or Cl-IB-MECA was added immediately upon reoxygenation following the ninety-minute hypoxic exposure. CCPA or Cl-IB-MECA was maintained in the media for an additional hour prior to determination of the percentage of myocytes killed. Although CCPA or Cl-IB-MECA was able to protect the myocytes when present during the reoxygenation, the extent of protection was small (% myocytes killed following the 90 minute hypoxia= 26.5±1.0%, n=6,±S.E. vs. CCPA present=22.1±1.5%, n=5 or vs. Cl-IB-MECA present=23.0±1.4%, n=5; ANOVA and t test, $P<0.05$) The previous example illustrates the efficacy of A3/A1 adenosine receptor agonists in reducing ischemic damage to the heart. A variety of other compounds have been developed which also stimulate A3 adenosine receptors. These are set forth below:

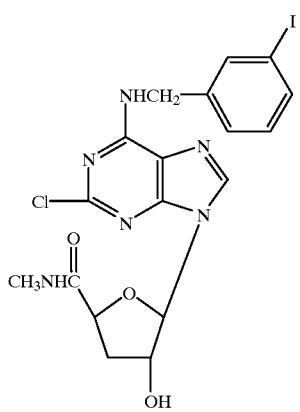

MRS 584

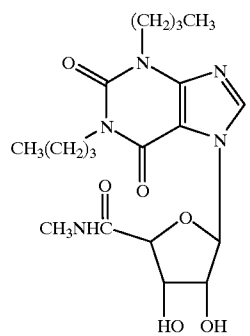

MRS 479

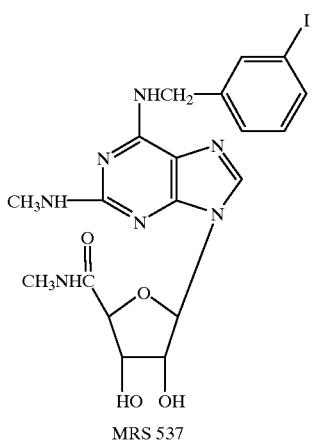

MRS 537

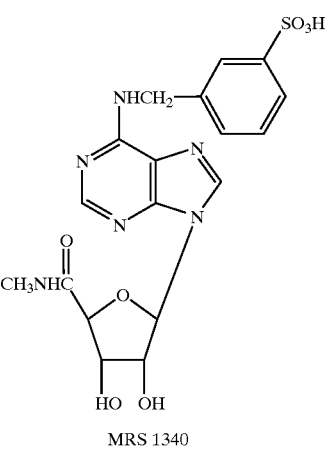

MRS 1340

Additional A3 selective agonists are set forth below:

A3 selective

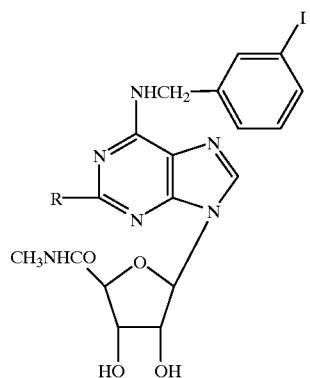

R = H, IB-MECA 54/56/1.1
R = Cl, Cl-IB-MECA 820/470/0.33

-continued

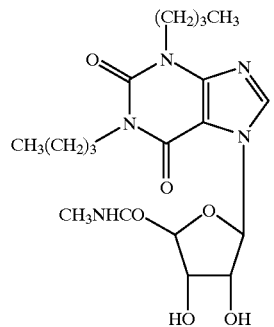

DBXMR 37,300/>100,00/229

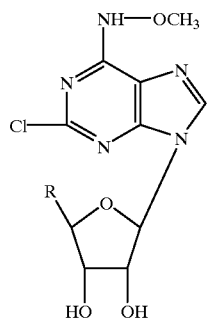

R = CH=CH₂, NNC21-D238 1230/83,400/20.2(h)
R = CH₂OCH₃, NNC53-0055 100/9500/4.8(h)

The compounds shown immediately above have been assayed for cardioprotective efficacy during prolonged ischemia in the in vitro culture system described in Example I.

Figure 3A:
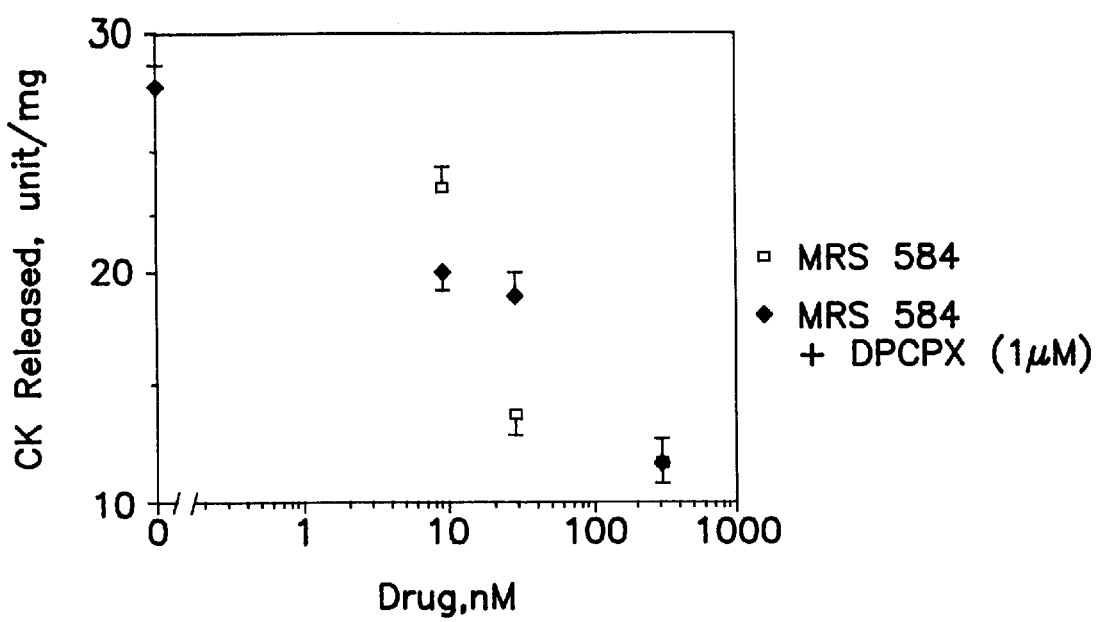
FIGS. 3A–3F are graphs illustrating the cardioprotective effects of the MRS compounds of the invention.
Figure 3B:
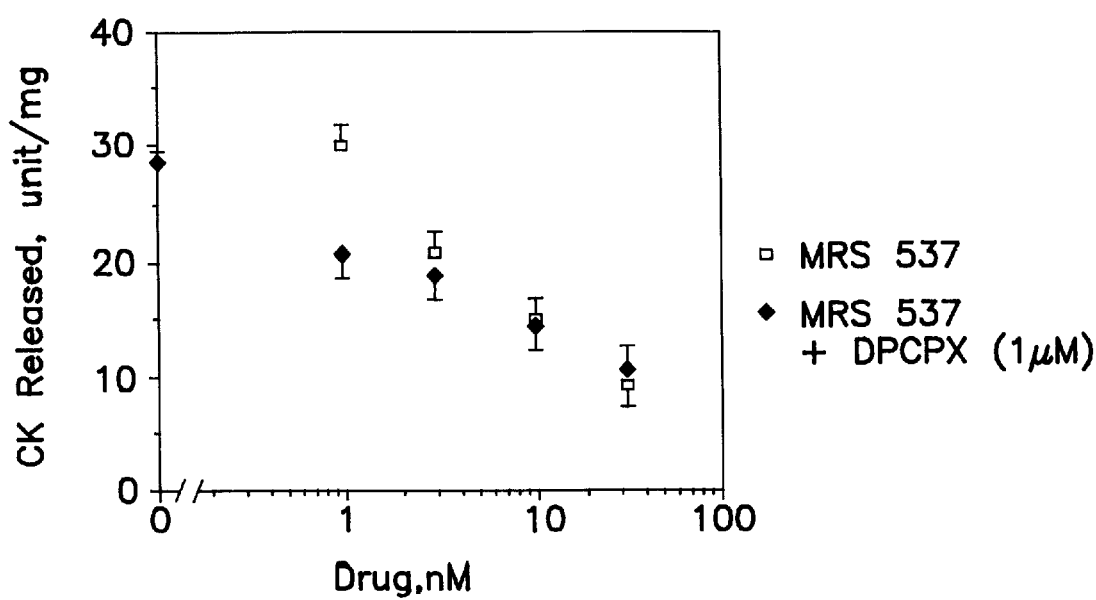
Figure 3C:
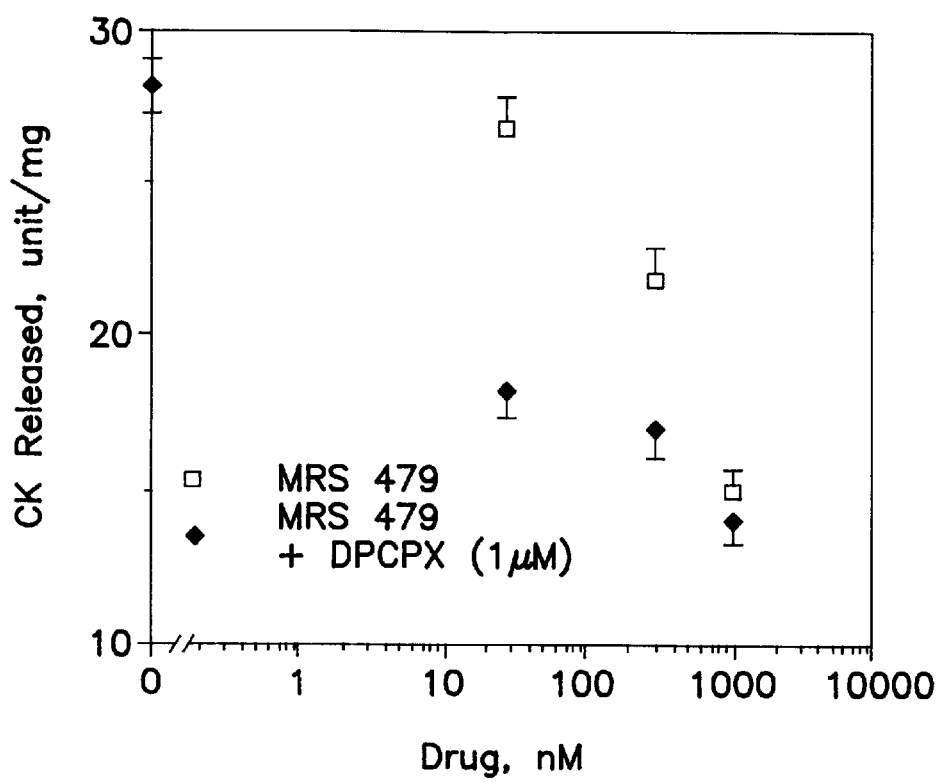
Figure 3D:
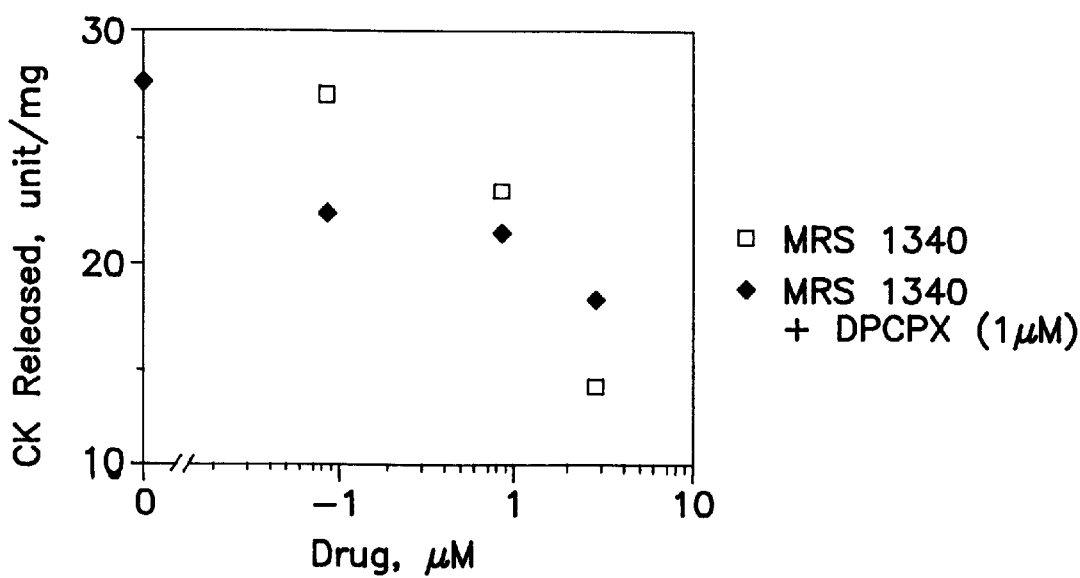

The cardioprotective effects of A3 receptor agonists MRS 584, MRS 537, MRS 479, MRS 1340 were assessed in the presence or absence of the A1 receptor antagonist DPCPX. The A1 receptor antagonist was utilized to demonstrate the selectivity of the MRS compounds for the A3 as opposed to the A1 adenosine receptor. FIG. 3A shows the cardioprotective effects of MRS 584 in the presence and absence of DPCPX. The extent of myocyte injury was plotted as the amount of creatine kinase released during the prolonged simulated ischemia. FIG. 3B shows the cardioprotective effects of MRS 537 in the presence and absence of DPCPX. The extent of myocyte injury was plotted as the amount of creatine kinase released during the prolonged simulated ischemia as a function of increasing the concentrations of MRS 537. FIG. 3C shows the cardioprotective effects of MRS 479 in the presence and absence of DPCPX. The extent of myocyte injury was plotted as the amount of creatine kinase released during the prolonged simulated ischemia as a function of increasing the concentrations of MRS 479. FIG. 3D shows the cardioprotective effects of MRS1340 in the presence and absence of DPCPX. The extent of myocyte injury was plotted as the amount of creatine kinase released during the prolonged simulated ischemia, as a function of increasing the concentrations of MRS1340.

To determine whether the protective effects of the compounds of the invention would also comparably stimulate the human adenosine A3 receptor, atrial cardiac myocytes, which express little if any endogenous A3 receptor, were transfected with either empty vector or vector containing the human adenosine A3 receptor cDNA. The transfected myocytes were then exposed to the compound for 5 minutes, which was followed by replacement with fresh media and myocytes exposed to normal conditions (non-ischemic) for 10 minutes prior to being exposed to ninety minutes of ischemia. The decrease in the number of myocytes killed in A3 receptor cDNA-transfected myocytes as compared to vector-transfected myocytes was plotted as a function of the concentration of the compound. This decrease in myocytes killed represented an index of the protection mediated via the human adenosine A3 receptor.

Figure 3E:
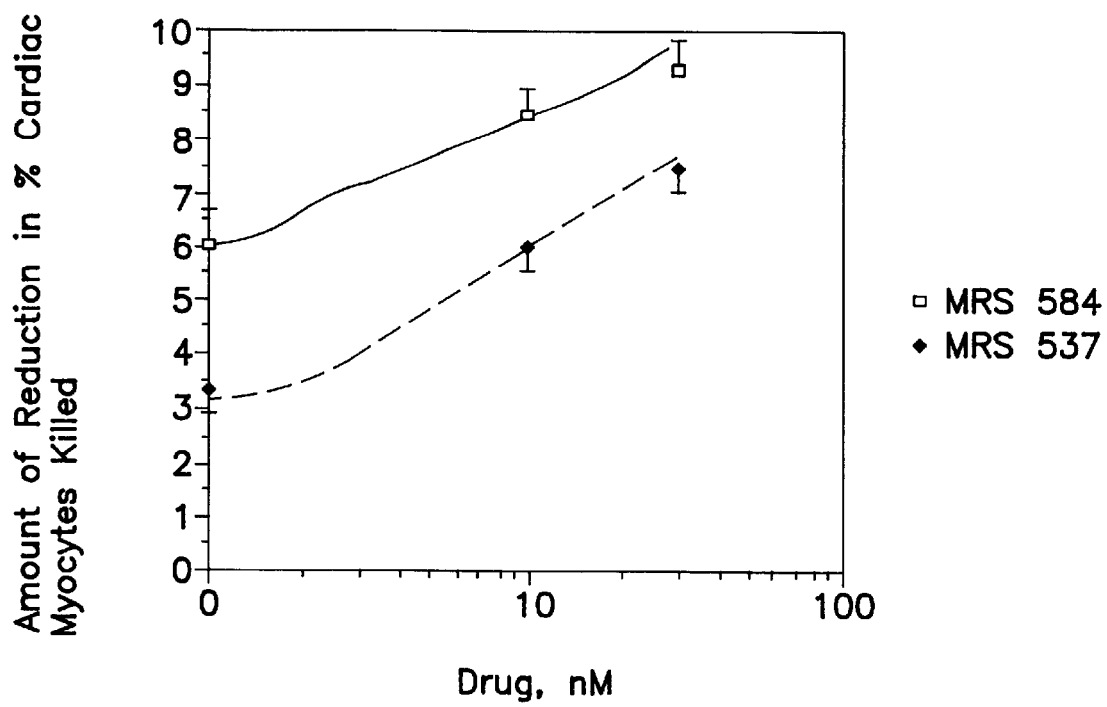

FIG. 3E shows the protective effects of MRS 584 and MRS 537 obtained when chick cells were transfected with a human A3 receptor encoded cDNA. These data show that the MRS compounds of the invention specifically bind to and activate the human A3 receptor.

Figure 3F:
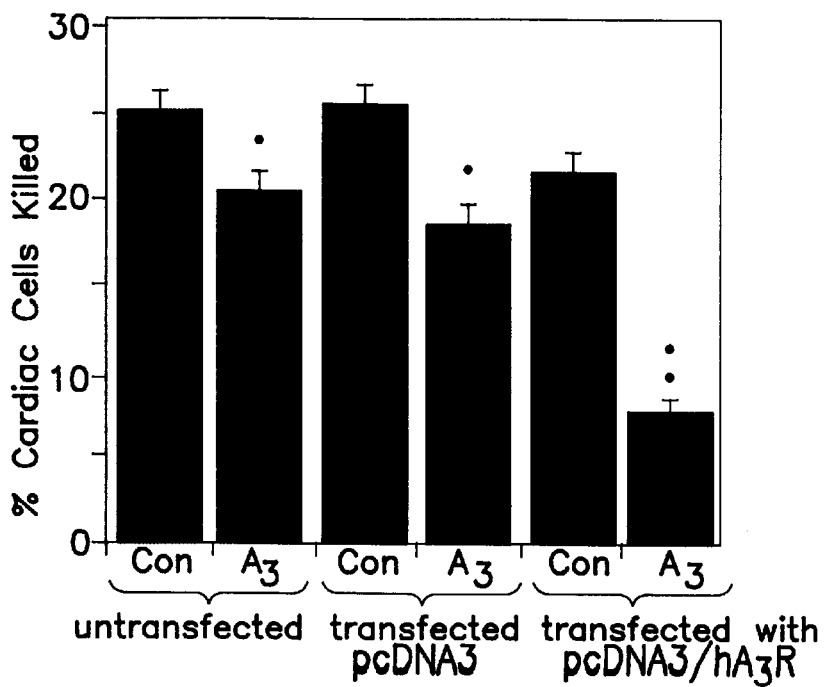

FIG. 3F shows that chick atrial cells aquire A3-receptor mediated cardioprotective responses upon transfection with human A3 receptor encoding cDNA. Cells were exposed to 10 nM Cl-IB-MECA and 1 $\mu$M DPCPX for five minutes. Media were replaced with fresh media lacking Cl-IB-MECA or DPCPX. Cells were then incubated under room air for thirty minutes prior to being exposed to 90 minutes of simulated ischemia. The graphs shows the results obtained in cells transfected with A3 receptor encoding cDNA, untransfected cells and cells transfected with empty vector. In untransfected cells or cells transfected with empty vector, the A3 agonist was able to reduce the percentage of cells killed when compared to cells not pre-exposed to A3 agonist (control cells, * t-test P<0.05). However, the A3 receptor mediated reduction in the number of cells killed or the amount of CK released, expressed as % decrease from those obtained in the control cells, was significantly greater in the cells transfected with the human A3 receptor encoding cDNA than in untransfected or cells transfected with empty vector (one-way ANOVA and t test P<0.01**)

These data illustrate that these compounds selectively activate human adenosine A3 receptor and can be used to prevent ischemic damage to the heart. Each of the above described MRS compounds is contemplated for use in combination with any of the A1 agonists described herein for reducing ischemic damage to the heart.

EXAMPLE II

ADENOSINE A1 AND A3 RECEPTOR AGONISTS ACT SYNERGISTICALLY TO INDUCE CARDIOPROTECTION

Adenosine can exert two principal cardioprotective effects. Adenosine can precondition the heart with reduction in the size of myocardial infarction (4,5,9,14,17,18). Intracoronary administration of adenosine during reperfusion following prolonged no-flow ischemia can also limit infarct size in the intact heart (1, 19). Our previous studies have characterized a cardiac myocyte model of injury, which is induced by exposure of myocytes to a prolonged period of hypoxia in glucose-free media (16, 23). Activation of either the A1 or the A3 receptor by their respective agonists can pharmacologically precondition the cardiac myocyte (23). FIGS. 1 and 2 show that the presence of A1 or A3 agonist can also protect the cardiac myocytes when the agonist is present individually during an actual injury-inducing ischemia.

Figure 4A:
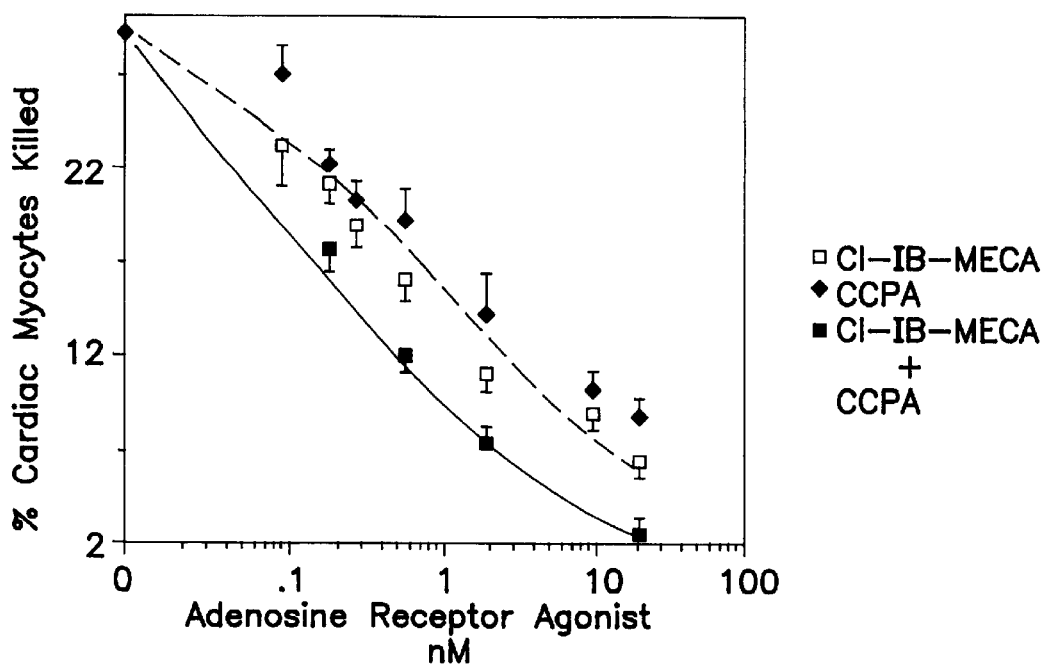
FIGS. 4A, and 4B are graphs showing the reduction in cardiac myocyte cell death following simultaneous exposure to A1 and A3 agonists on cardiac cells.
Figure 4B:
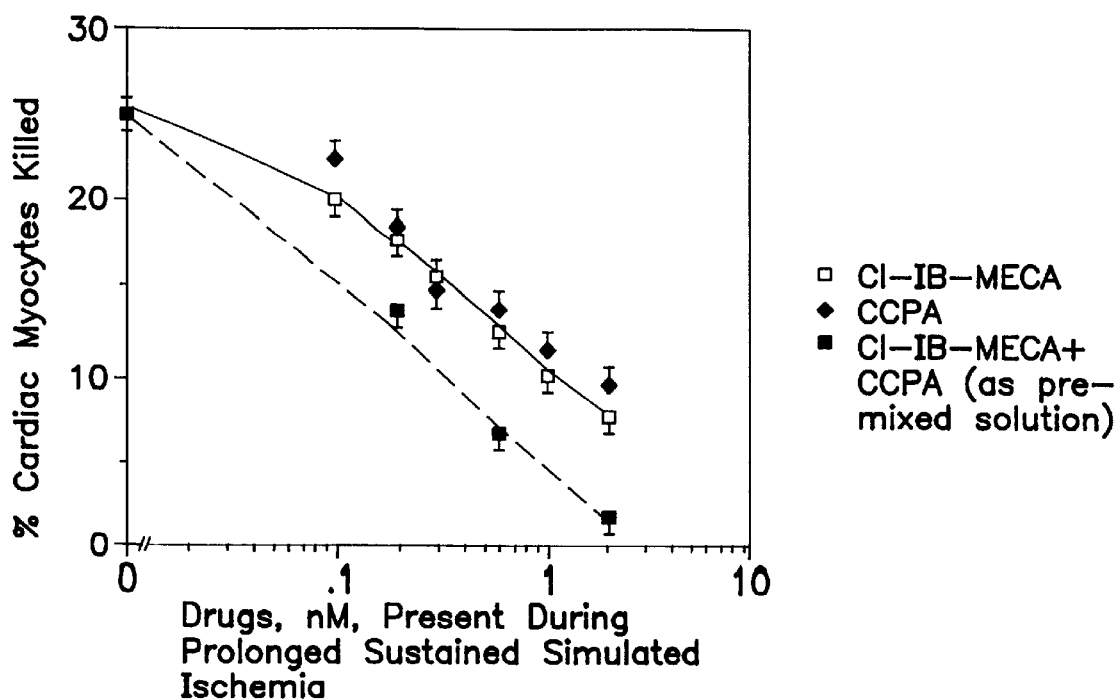

FIG. 4A shows that the simultaneous activation of both A1 and A3 receptors produces a greater preconditioning effect than when either receptor is activated separately. Thus, an A1 agonist and an A3 agonist interact synergistically to precondition the cardiac myocyte. In addition, the simultaneous presence of A1 and A3 receptor agonists during injury-producing ischemia resulted in less myocyte injury than when only A1 or A3 agonist is present. See FIG. 4B.

Thus, simultaneous administration of A1 and A3 agonists will lead to enhanced cardioprotection.

Based on the data presented above, it is apparent that a variety of A1 agonists and A3 agonists may be used in conjunction to reduce or prevent ischemic damage to the heart. Suitable A1 agonists contemplated for use in the present invention are set forth below in Table I.

TABLE I

A1 AGONISTS
$A_1$ selective

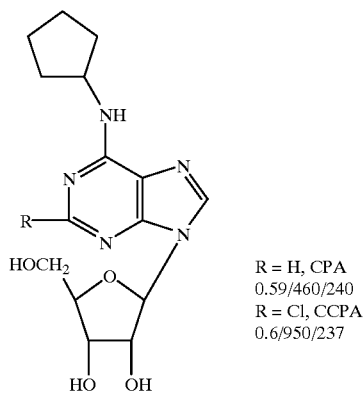

R = H, CPA
0.59/460/240
R = Cl, CCPA
0.6/950/237

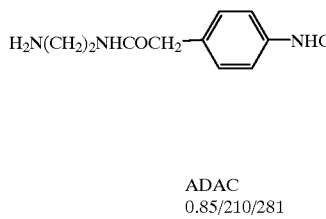

ADAC
0.85/210/281

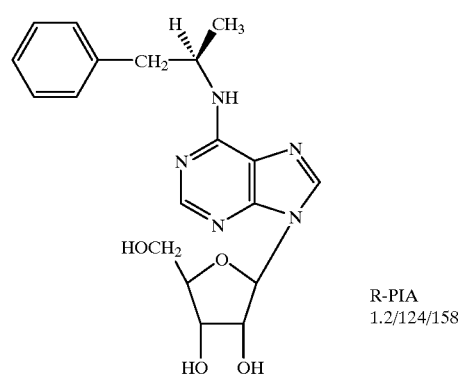

R-PIA
1.2/124/158

TABLE I-continued

A1 AGONISTS
$A_1$ selective

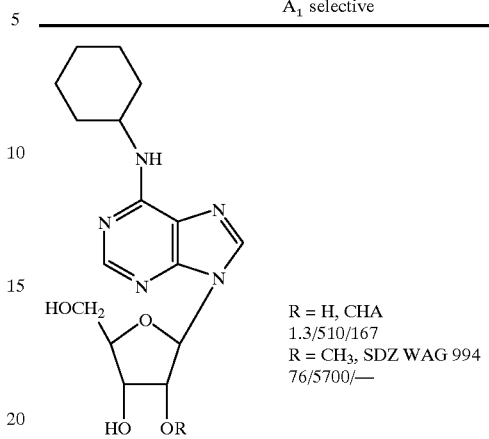

R = H, CHA
1.3/510/167
R = CH$_3$, SDZ WAG 994
76/5700/—

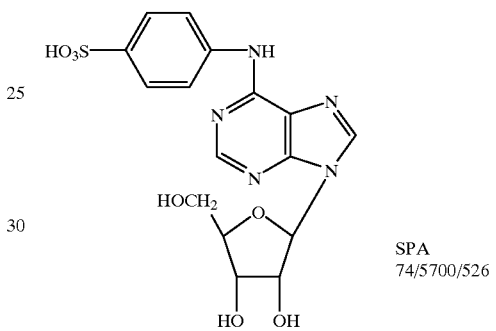

SPA
74/5700/526

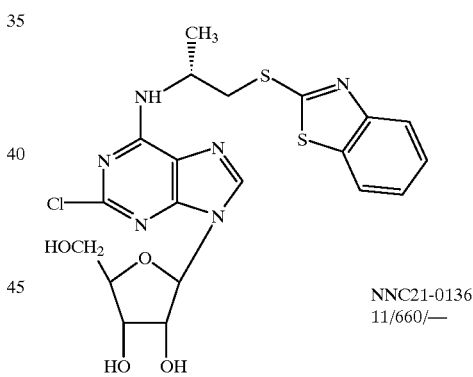

NNC21-0136
11/660/—

EXAMPLE III

CARDIOPROTECTIVE EFFECT OF AGONISTS ACTIVATING BOTH A1 AND A3 RECEPTORS

In yet another embodiment of the invention, the administration of an agonist capable of activating both A1 and A3 receptors will be used in the methods of the invention for reducing ischemic damage to the heart. Referred to herein as a mixed A3/A1 agonist, these agents mediate superior cardioprotective effects. Examples of mixed A3/A1 agonists that may also be used in the practice of the present invention are listed in Table II.

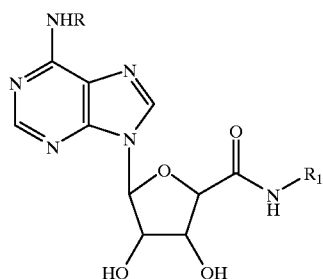

| COMPOUND (Reference) | R₁ | R | $A_1$ (nm) | $A_{2a}$ (nm) | $A_3$ (nm) |
|---|---|---|---|---|---|
| Compound 4q (Reference 27) MRS 646 | Ethyl | 3-iodophenyl acetamido | 16 | 3940 | 30 |
| Compound 4d (Reference 27) | Ethyl | 2-trifluoromethylphenyl acetamido | 384 | >10,000 | 54 |
| Compound 37 (Reference 8) | Ethyl | 4-nitrophenylethyl | 49 | 574 | 9.0 |
| Compound 11 (Reference 28) | Methyl | phenoxy | 2060 | 66,300 | 1340 |
| $N^6$-cyclohexyl NECA (Reference 29) | Ethyl | cyclohexyl | 0.43 | 170 | 16 |

4q = $N^6$-((3-iodophenyl)carbamoyl)adenosine-5'-uronamide
4d = $N^6$-((2-trifluoromethyl)carbamoyl)adenosine-5'-uronamide
compound 37 = $N^6$-(4-Nitrobenzyl)adenosine-5'-N-ethyluronamide
compound 11 = 6-(O-Phenylhydroxylamino)purine-9-beta-ribofuranoside-5'-N-methyluronamide
$N^6$-cyclohexyl NECA = $N^6$-cyclohexyl 5'-N-ethylcarboxamidoadenosine

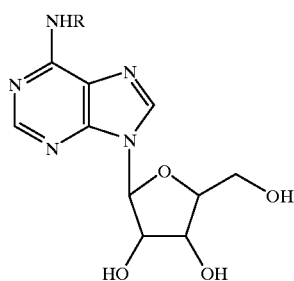

| COMPOUND | R = | $A_1$ (nM) | $A_2$ (nM) | $A_3$ (nM) |
|---|---|---|---|---|
| Compound 8* | 2-aminoethyl)amino]carbonyl]methyl]-anilino]carbonyl]methyl]phenyl | 0.85 | 210 | 4 |

*$N^6$-[[[4-[2-aminoethyl)amino]carbonyl]methyl -anilino]carbonyl]methyl]phenyl]adenosine Other examples of mixed A1/A3 agonists are MRS 580 and MRS 1364, the structures of which are shown below.

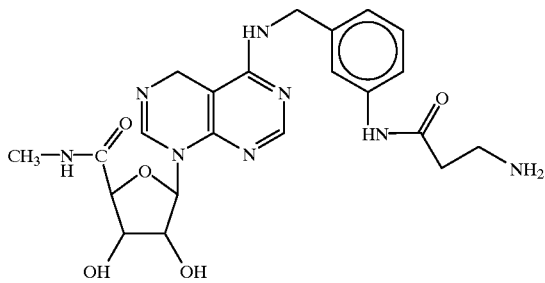

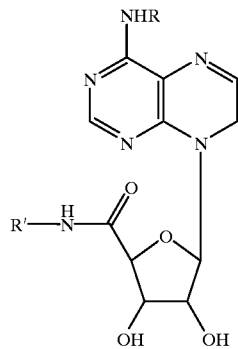

MRS 1364
R' = Et
R = CONH-phenyl-$NO_2$

Figure 5A:
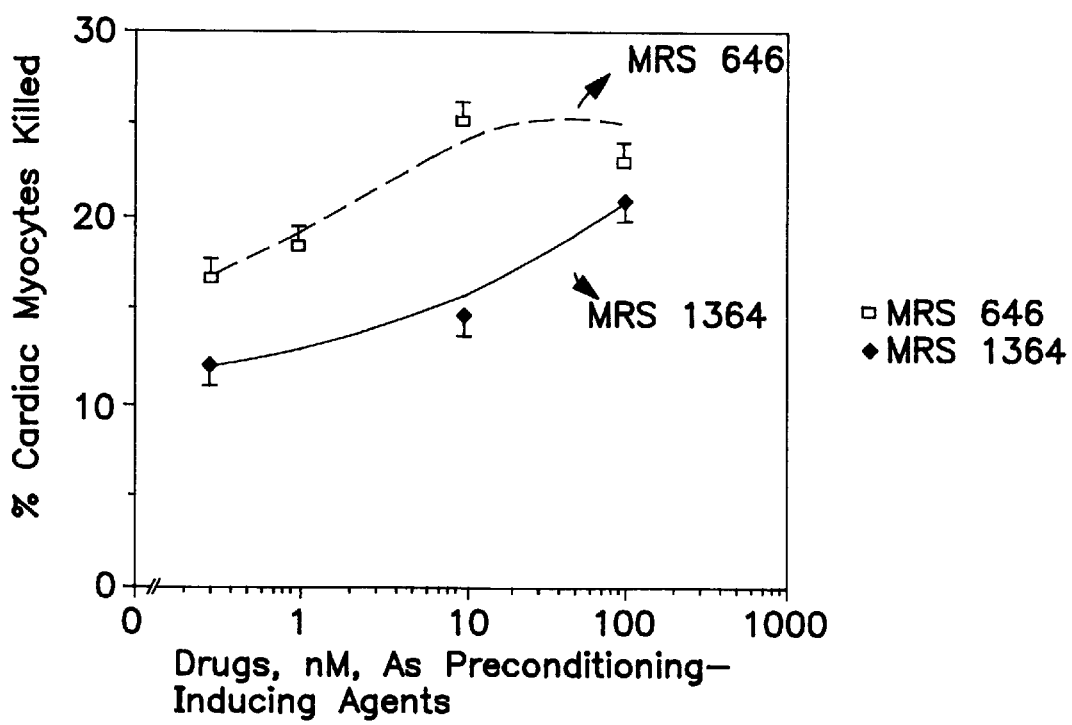
FIGS. 5A–5D are graphs showing the cardioprotective effects mediated by MRS 646 and MRS 1364 which activate the A1 and A3 receptors simultaneously.

FIG. 5A shows the results obtained when ventricular myocytes were exposed to the indicated concentrations of MRS646 (structure 4Q, table II) or MRS1364 for 5 minutes. Media were then replaced with fresh media, which was then followed by exposure to 90-minute simulated ischemia and the data graphed. The data show that these mixed A3/A1 agonists can pharmacologically induce preconditioning in cardiac myocytes.

Figure 5B:
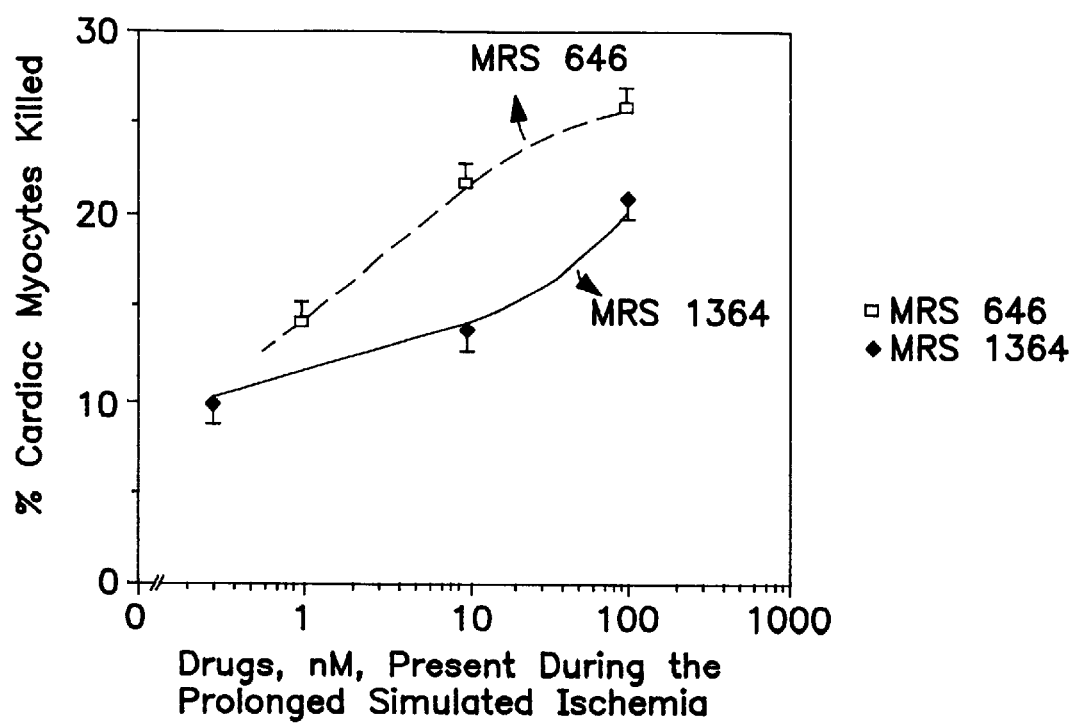
Figure 5C:
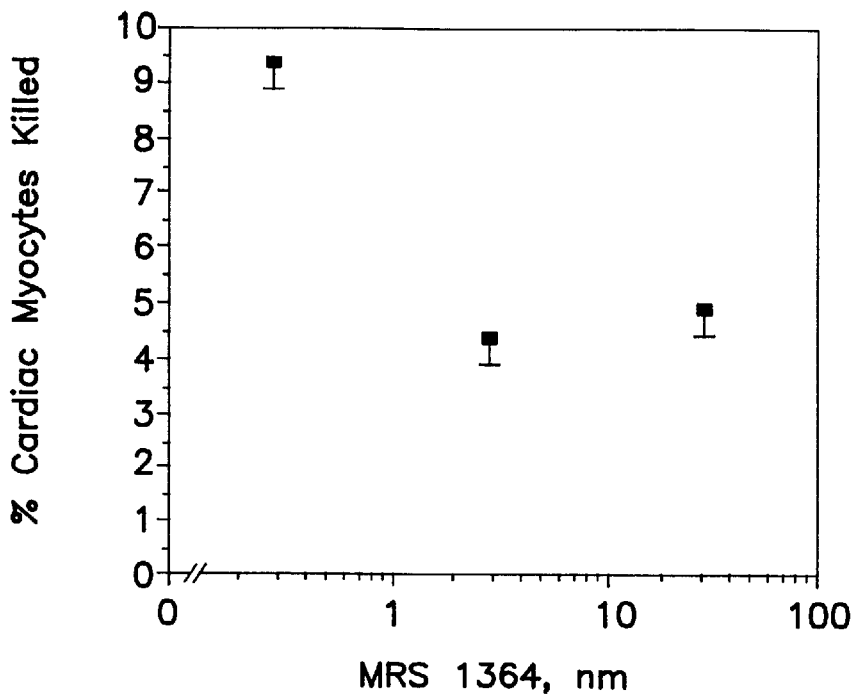
Figure 5D:
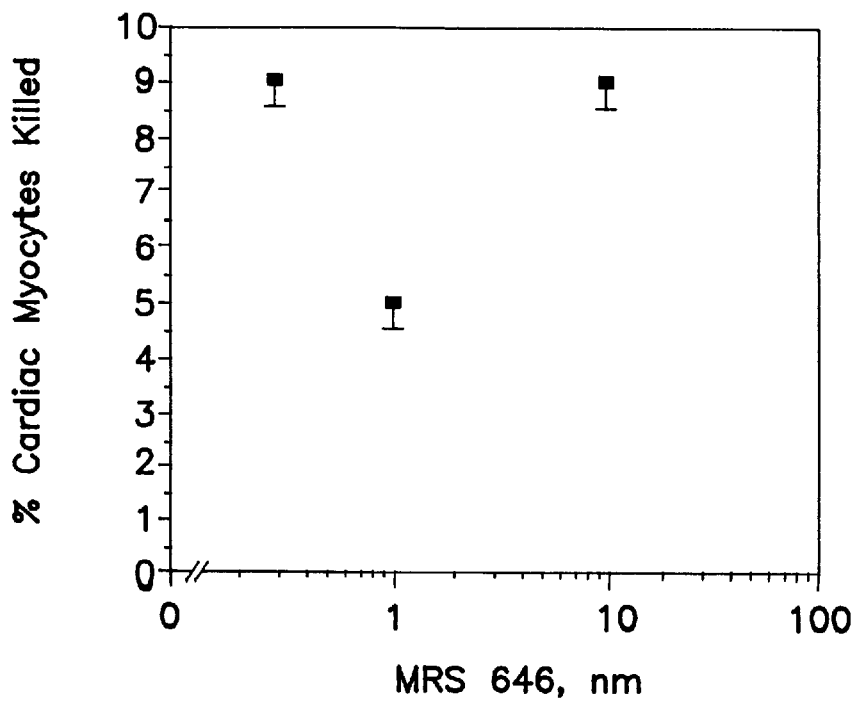

FIG. 5B shows that MRS 646 and MRS 1364 also potently protect against myocyte injury during the sustained simulated ischemia. FIGS. 5C and 5D show that these agonists can pharmacologically precondition the cardiac myocyte and induce potent cardioprotection via the human adenosine A3 receptor.

Figure 6A:
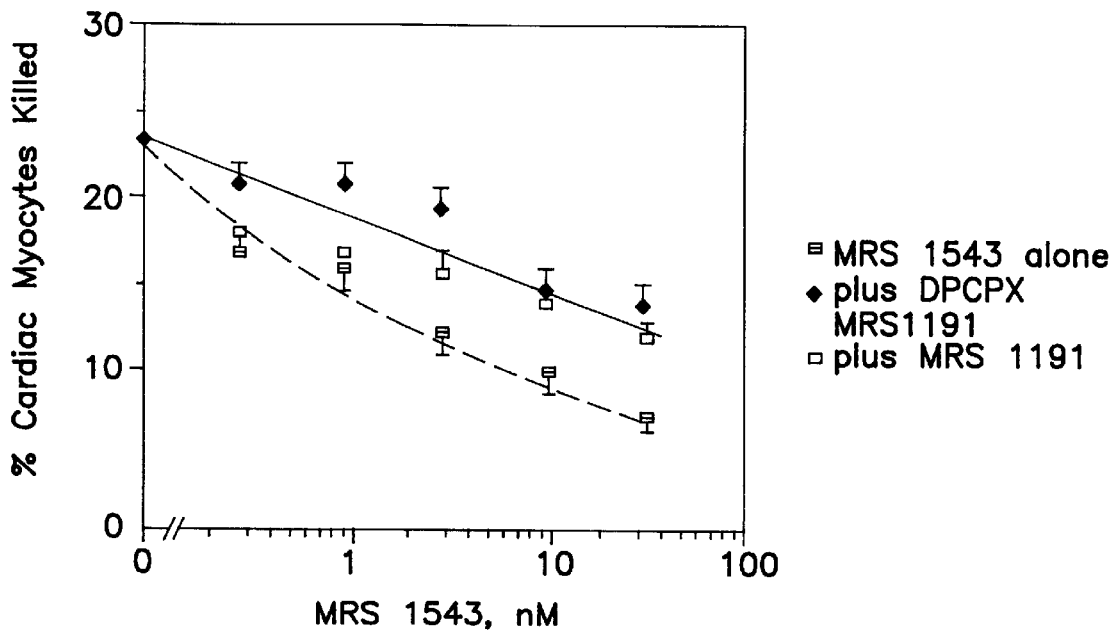
FIGS. 6A, 6B and 6C are graphs that show the cardioprotective effects of MRS1543, a binary A1/A3 agonist.
Figure 6B:
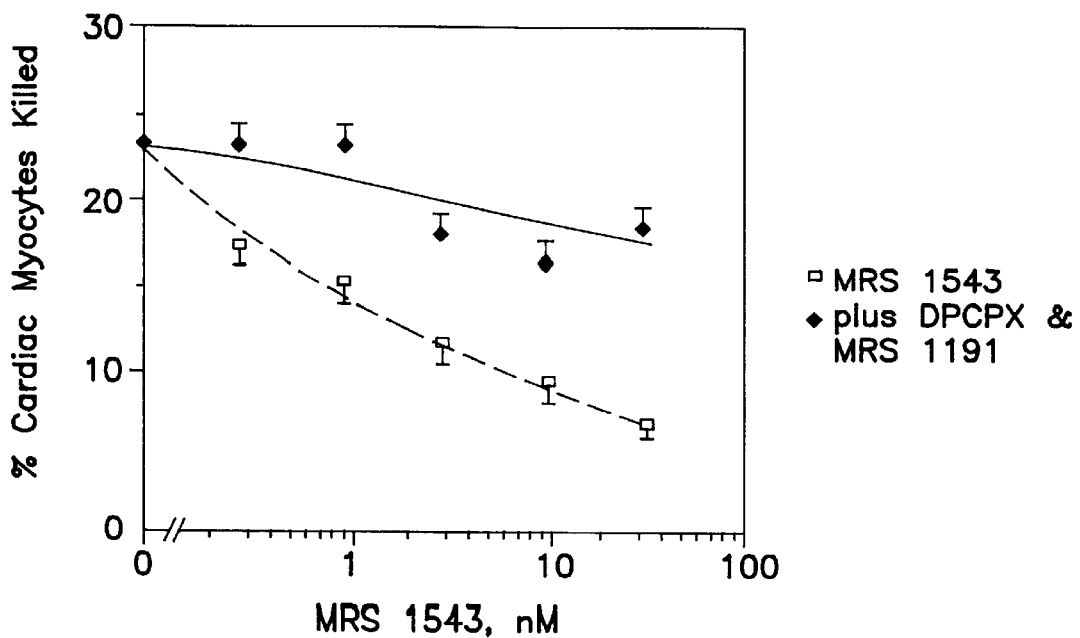
Figure 6C:
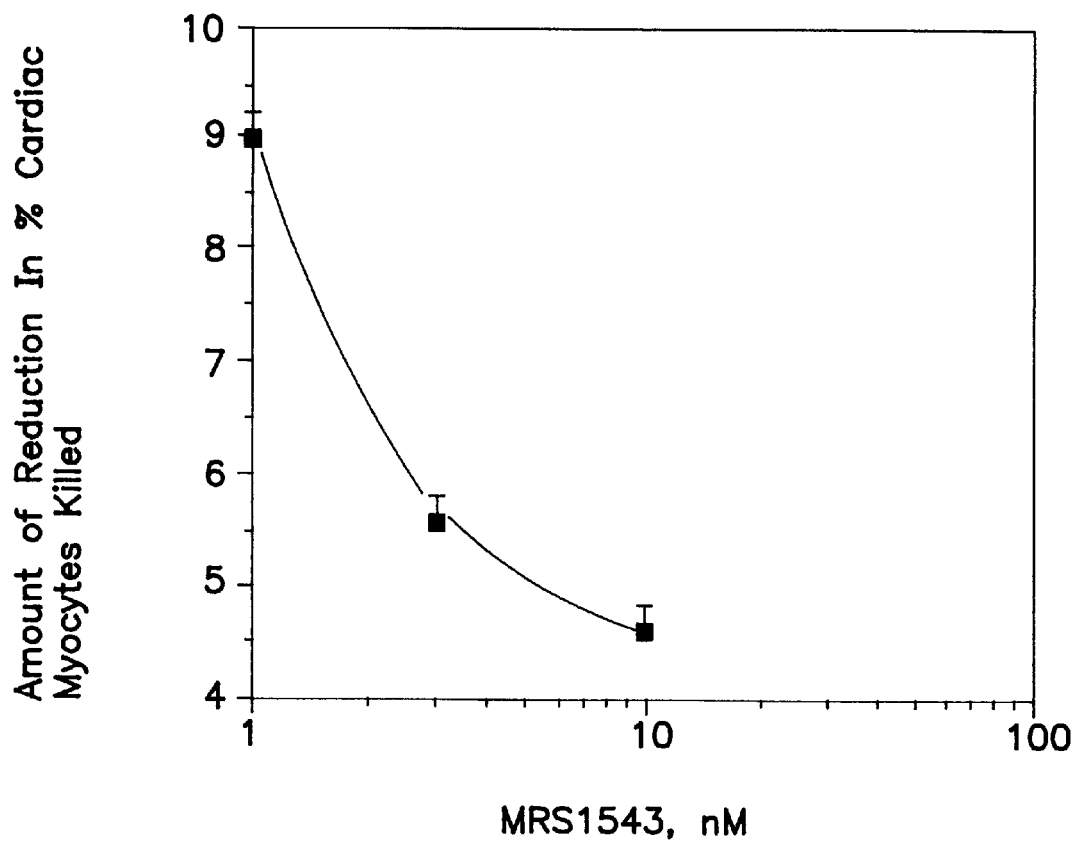

In yet another embodiment of the invention, a binary conjugate has also been synthesized which binds and activates both the A1 and A3 receptors simultaneously. FIG. 6A shows that this binary conjugate, MRS1543, can pharmacologically precondition the cardiac myocyte and induce a potent cardioprotective effect. The protective effect is only partially blocked by A1 antagonist DPCPX; similarly, the protection is only partially attenuated by the A3 antagonist MRS1191. FIG. 6B shows, however, that the combined presence of DPCPX and MRS1191 completely abolished the protective effect of MRS1543, indicating that the protection is mediated via activation of both the A1 and the A3 receptors. FIG. 6C shows that MRS1543 can precondition and induces a cardioprotective effect via the human adenosine A3 receptor.

EXAMPLE IV

SIMULTANEOUS ADMINISTRATION OF A3/A1 ADENOSINE RECEPTOR AGONIST AND ADENOSINE A2a RECEPTOR ANTAGONIST GIVES RISE TO ENHANCED CARDIOPROTECTION

In yet another embodiment of the invention the simultaneous administration of A3 and A1 adenosine receptor agonist and A2a antagonist is contemplated. Preferred A2a adenosine receptor antagonists for use in the present invention are listed below in Table III:

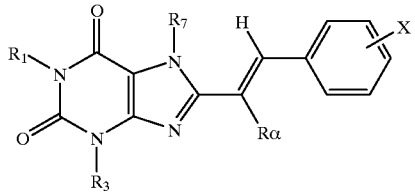

R1, R3=methyl, ethyl, propyl, allyl
R7=H, methyl, alkyl (C2–C8)
Rα=H (unless noted)
X=is shown in Table III

TABLE III

Affinities of 8-Styrylxanthine Derivatives in
Radioligand Binding Assays at Rat Brain $A_1$ and $A_2$-Receptors (31)

| cmpd | $R_1-R_3$ | $R_7$ | X | $A_1/A_2$ ratio |
|---|---|---|---|---|
| 15b | Me | Me | H | 41 |
| 17b | Me | Me | 2-MeO | 18 |
| 19b | Me | Me | 3-MeO | 64 |
| 20b | Me | Me | 3-$CF_3$ | 25 |
| 21b | Me | Me | 3-$NO_2$ | 11 |
| 22b | Me | Me | 3-$NH_2$ | 30 |
| 23 | Me | Me | 3-(AcNH) | 240 |
| 24 | Me | Me | 3-(HOOC($CH_2$)$_2$CONH) | 250 |
| 25 | Me | Me | 3-(t-BOC-NH) | 30 |
| 26 | Me | Me | 3-[t-BOC)$_2$N] | 15 |
| 27b | Me | Me | 3-F | 190 |
| 28 | Me | Me | 3-Cl | 520 |
| 29b | Me | Me | 4-MeO | 44 |
| 32b | Me | Me | 3,4-(MeO)$_2$ | 70 |
| 33a | Me | H | 3,5-(MeO)$_2$ | 25 |
| 33b | Me | Me | 3,5-(MeO)$_2$ | >200 |
| 34b | Me | Me | 3,5-$F_2$ | 230 |
| 35 | Me | Me | 3,5-(MeO)$_2$-4-OH | 19 |

TABLE III-continued

Affinities of 8-Styrylxanthine Derivatives in
Radioligand Binding Assays at Rat Brain $A_1$ and $A_2$-Receptors (31)

| cmpd | $R_1$–$R_3$ | $R_7$ | X | $A_1/A_2$ ratio |
|---|---|---|---|---|
| 36 | Me | Me | 4-AcO-3,5-(MeO)$_2$ | 93 |
| 37 | Me | Me | 4-(4-PhCH$_2$O)-3,5-(MeO)$_2$ | 30 |
| 38 | Me | Me | 4-(4-NH$_2$BuO)-3,5 (MeO)$_2$ | 36 |
| 39 | Me | Me | 4-[4-(tBOC—NH)BuO]-3,5-(MeO)$_2$ | 42 |
| 40 | Me | Me | 4-(4-NH$_2$-trans-CH$_2$CH=CHCH$_2$O-3,5-(MeO)$_2$ | 28 |
| 41 | Me | Me | 4-(4-AcNH-trans-CH$_2$CH=CH$_2$O)-3,5-(MeO)$_2$ | >50 |
| 42 | Me | Me | 4-(4-t-BOC-NH-trans-CH$_2$CH=CHCH$_2$O)-3,5-(MeO)$_2$ | >40 |
| 43b | Me | Me | 2,3,4-(MeO)$_3$ | 34 |
| 44b | Me | Me | 3,4,5-(MeO)$_3$ | 70 [>5600] |
| 45b | Et | Me | 3,4,5-(MeO)$_3$ | 34 |
| 46 | allyl | Me | 3,4,5-(MeO)$_3$ | 13 [>6700] |
| 51b | Pr | Me | 3-Cl | 14 |
| 52b | Pr | Me | 3,4-(MeO)$_2$ | 19 [190] |
| 53b | Pr | Me | 3,5-(MeO)$_2$ | 110 |

Additional compounds contemplated for use as $A_{2a}$ antagonists include:

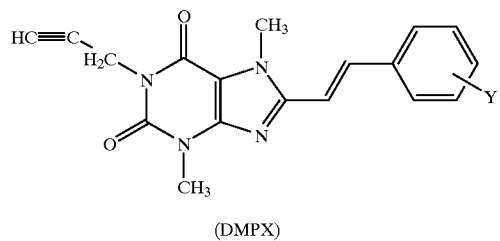

(DMPX)

Y = m-Br or p-SO$_3$H

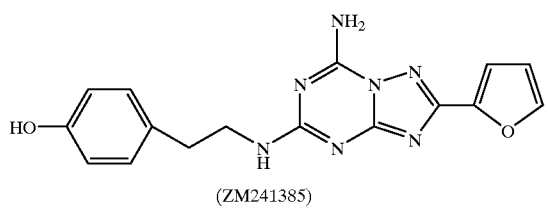

(ZM241385)

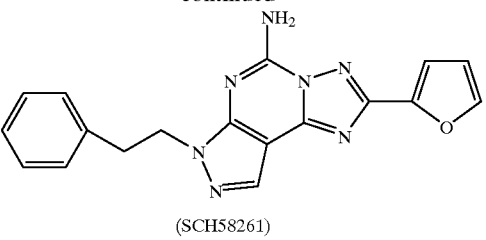

(SCH58261)

Figure 7A:
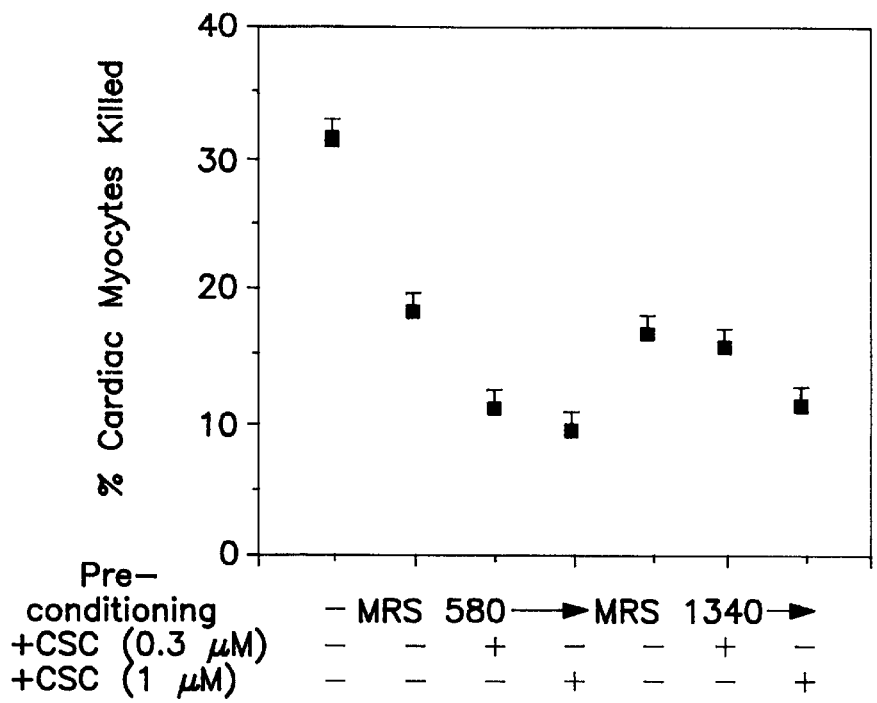
FIGS. 7A and 7B are graphs showing the cardioprotective effects of simultaneous administration of an A3/A1 agonist, MRS 580, and an $A_{2a}$ antagonist on myocyte survival.
Figure 7B:
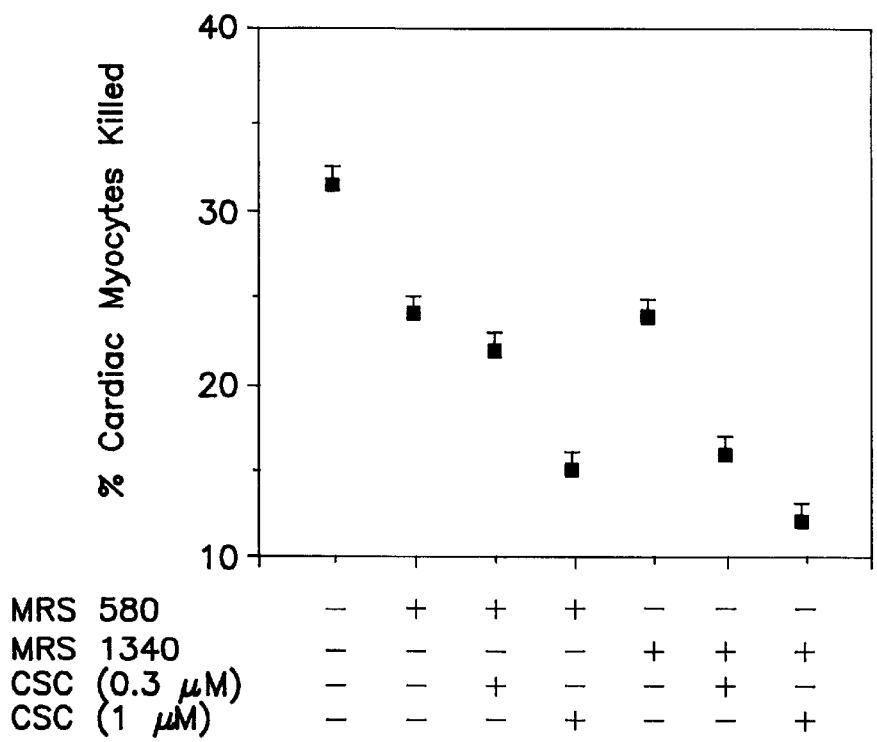
Figure 7C:
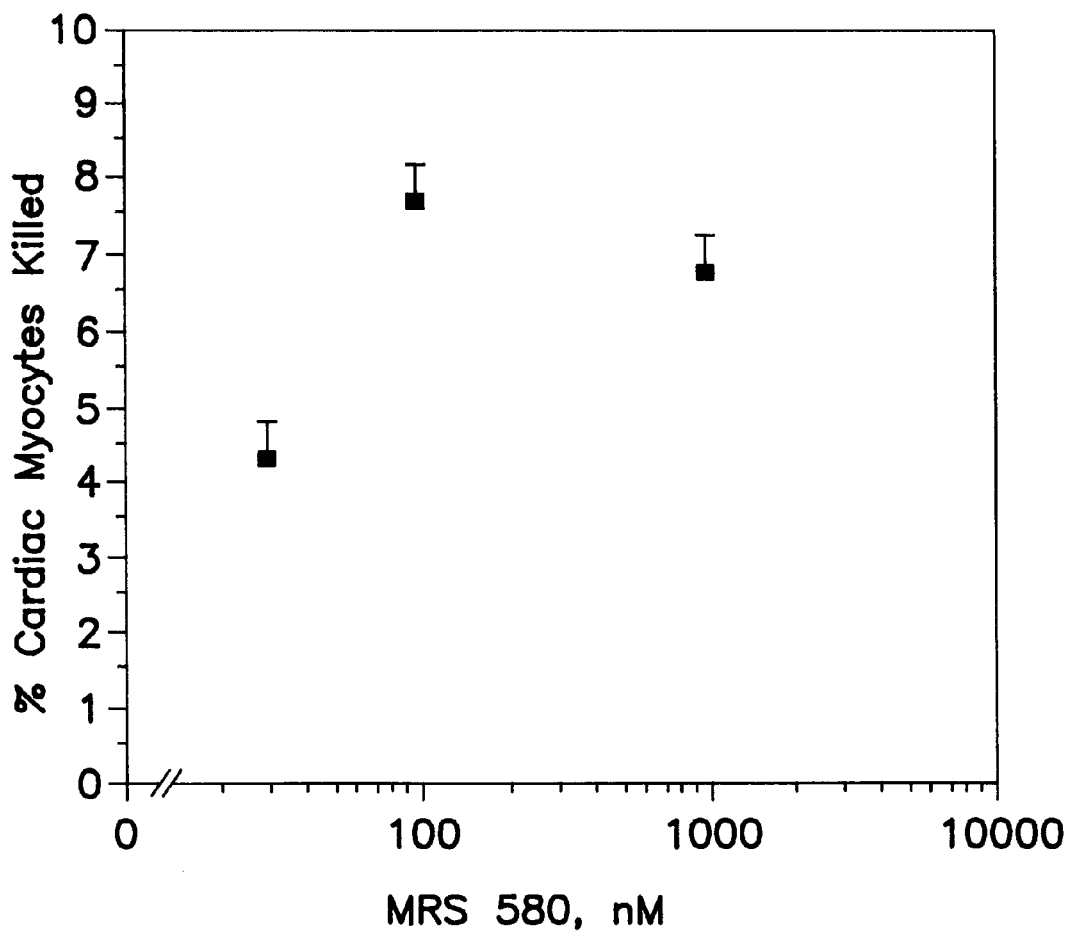
FIG. 7C shows that MRS 580 can also precondition the cardiac myocyte via the human adenosine A3 receptor.

The results shown in FIGS. 7A and 7B indicate that the simultaneous administration of an A3/A1 agonist and an A2a antagonist gives rise to enhanced cardioprotection. Cardiac myocytes were prepared as described in Example I. The A1/A3 agonist, MRS 580, was delivered in the presence or absence of the A2a antagonist CSC. Data were plotted as the percentage of cells killed vs. the various drug combinations as indicated. Data represent the means±S.E. of three experiments. FIG. 7C shows that MRS 580 can precondition the cardiac myocytes via the human adenosine A3 receptor.

Figure 8A:
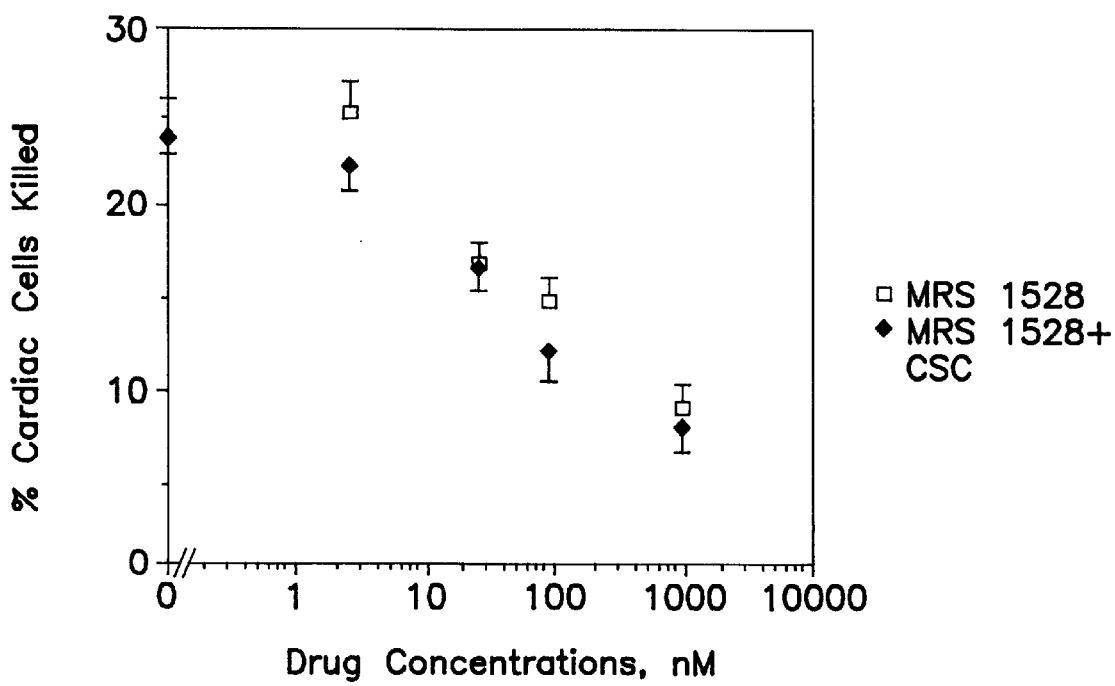
FIGS. 8A–8E are a series of graphs showing the cardioprotective effects of MRS1528, a binary conjugate having agonist activity at the A3 receptor and antagonist activity at the A2a receptors.
Figure 8B:
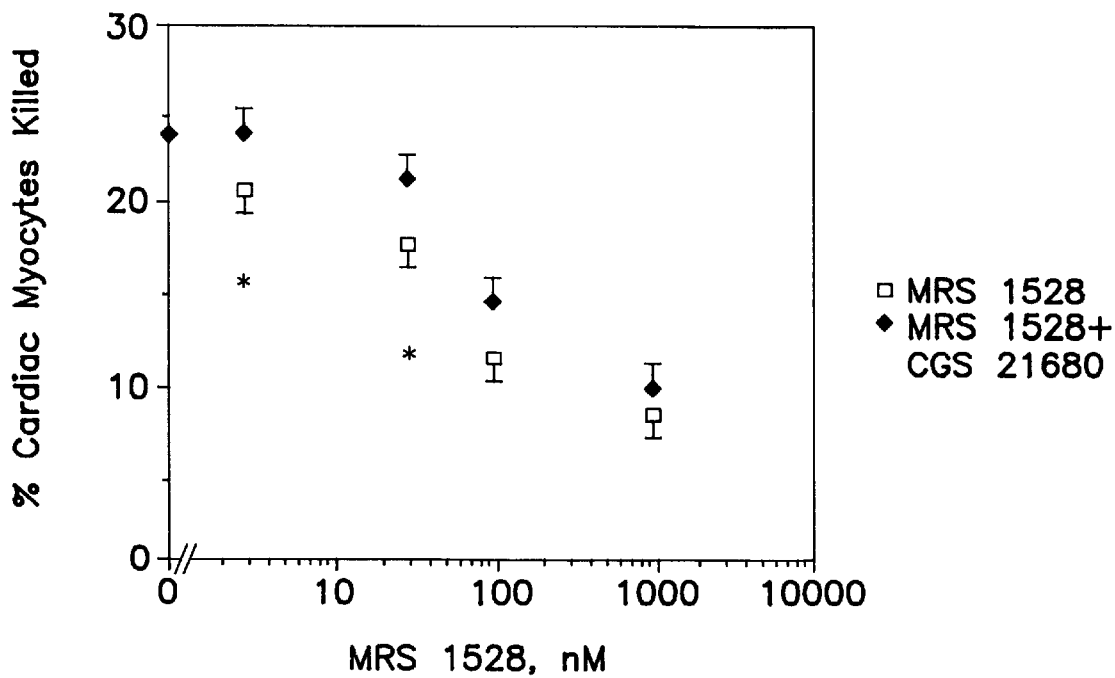
Figure 8C:
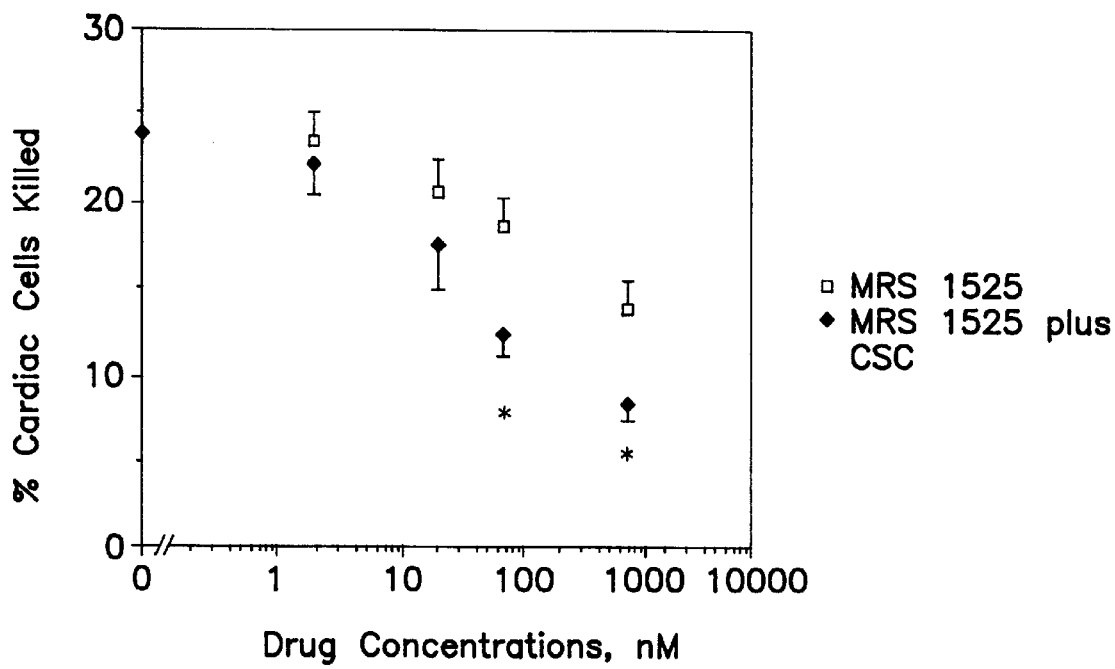
Figure 8D:
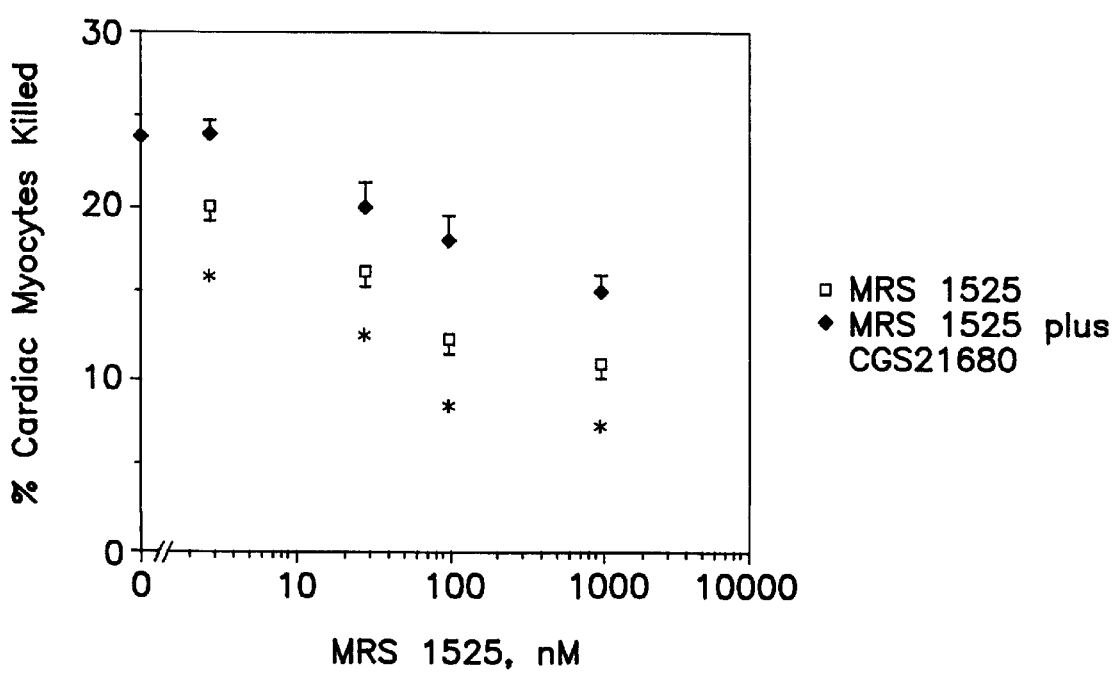
Figure 8E:
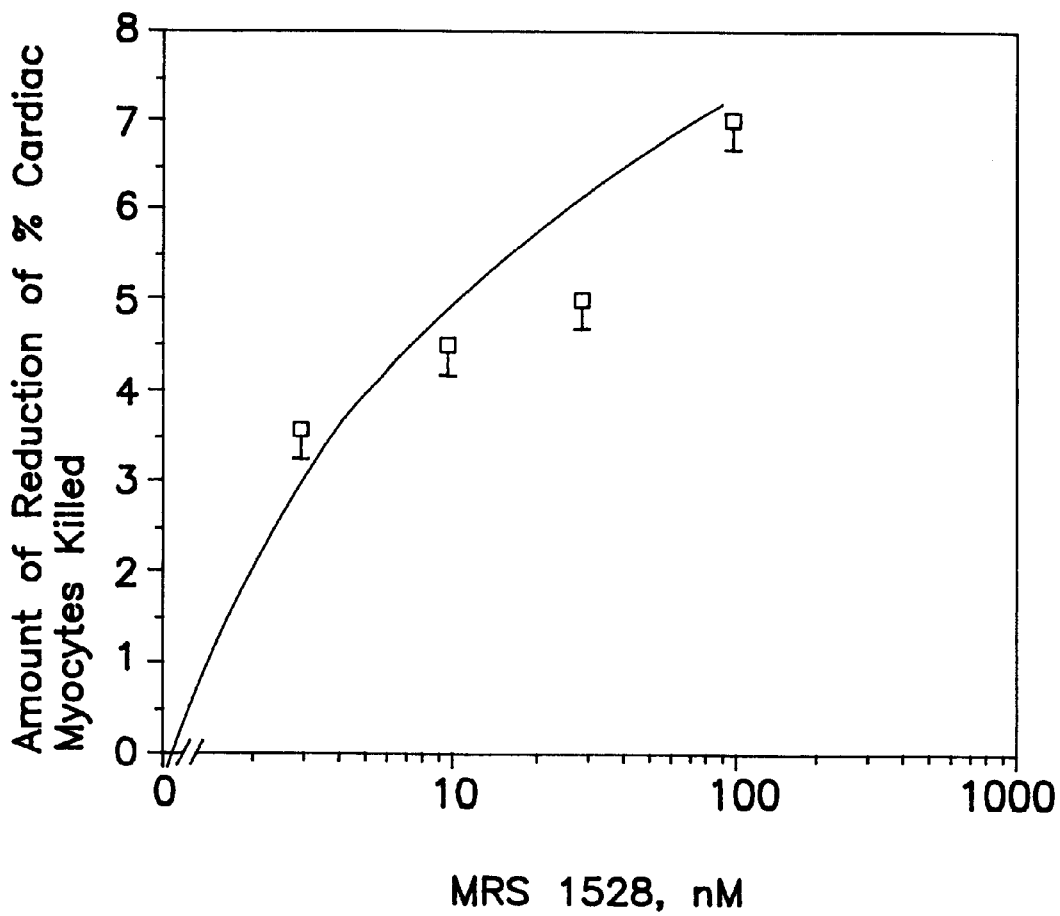

In another embodiment, a binary conjugate, MRS 1528, was synthesized which acts as an agonist at the A3 receptor and an antagonist at the A2a receptor simultaneously. FIG. 8A shows that the protective effect of MRS1528 was unaffected by the A2a receptor antagonist CSC, consistent with the ability of MRS1528 to block the A2a receptor. FIG. 8B shows that the protective effect of low concentrations of MRS1528 is attenuated by the A2a agonist CGS21680 whereas the protective effect of high concentrations of MRS1528 is not affected by the presence of CGS21680. Together, these data indicate that MRS1528 can activate A3 receptor to induce preconditioning and can simultaneously block the A2a receptor to enhance its preconditioning effect. Further support for this concept comes from studies testing the A3 agonist moiety of MRS1528, MRS1525. MRS1525 does not contain the A2a antagonist moiety and in response to the CSC, showed a uniform CSC-mediated increase in the extent of preconditioning effect (FIG. 8C). In the concomitant presence of CGS21680, the preconditioning effect of MRS1525 is attenuated at both the high and low concentrations of MRS1525 (FIG. 8D). FIG. 8E shows that MRS1528 can cause preconditioning of the cardiac myocytes via human adenosine A3 receptor.

A binary conjugate was synthesized with the general structure shown below. This conjugate binds both the A2a and the A3 receptors and acts as an agonist at the A3 receptor and an antagonist at the A2a receptor simultaneously. In the exemplary conjugate disclosed herein, MRS 1528, R=H and n=2. A3/A2a binary conjugate

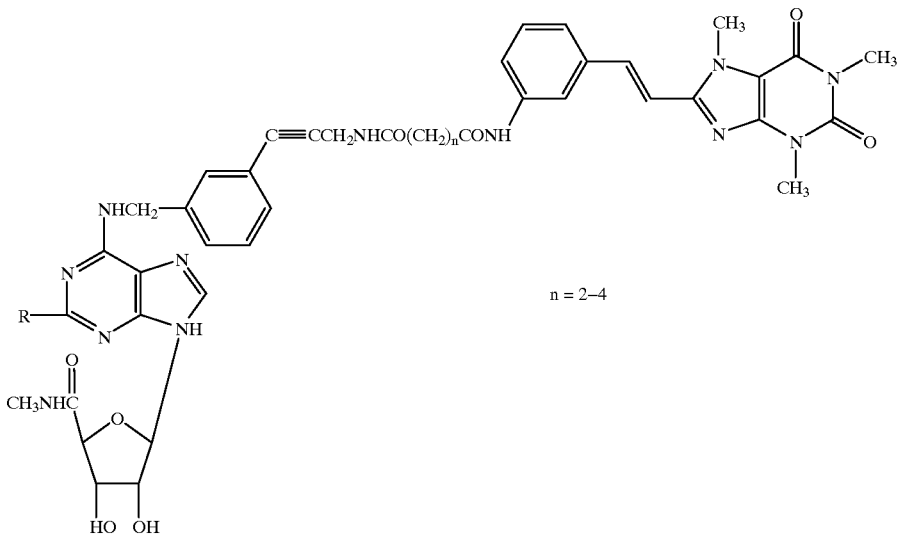

A3/A2a Binary conjugate R=H, IB-MECA; R=Cl, Cl-IB-MECA

A second binary conjugate has also been synthesized which binds and activates both the A1 adenosine and A3 adenosine receptors simultaneously and has the general structure shown below. In an exemplary A1/A3 binary conjugate of the invention, MRS 1543, R=H.

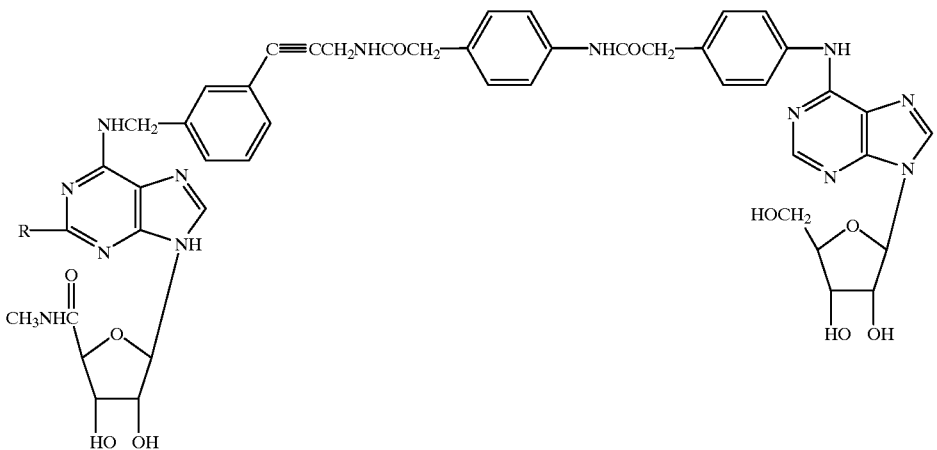

A3/A1 binary conjugate
R=H, IB-MECA
R=Cl, CL-IB-MECA

Figure 9:
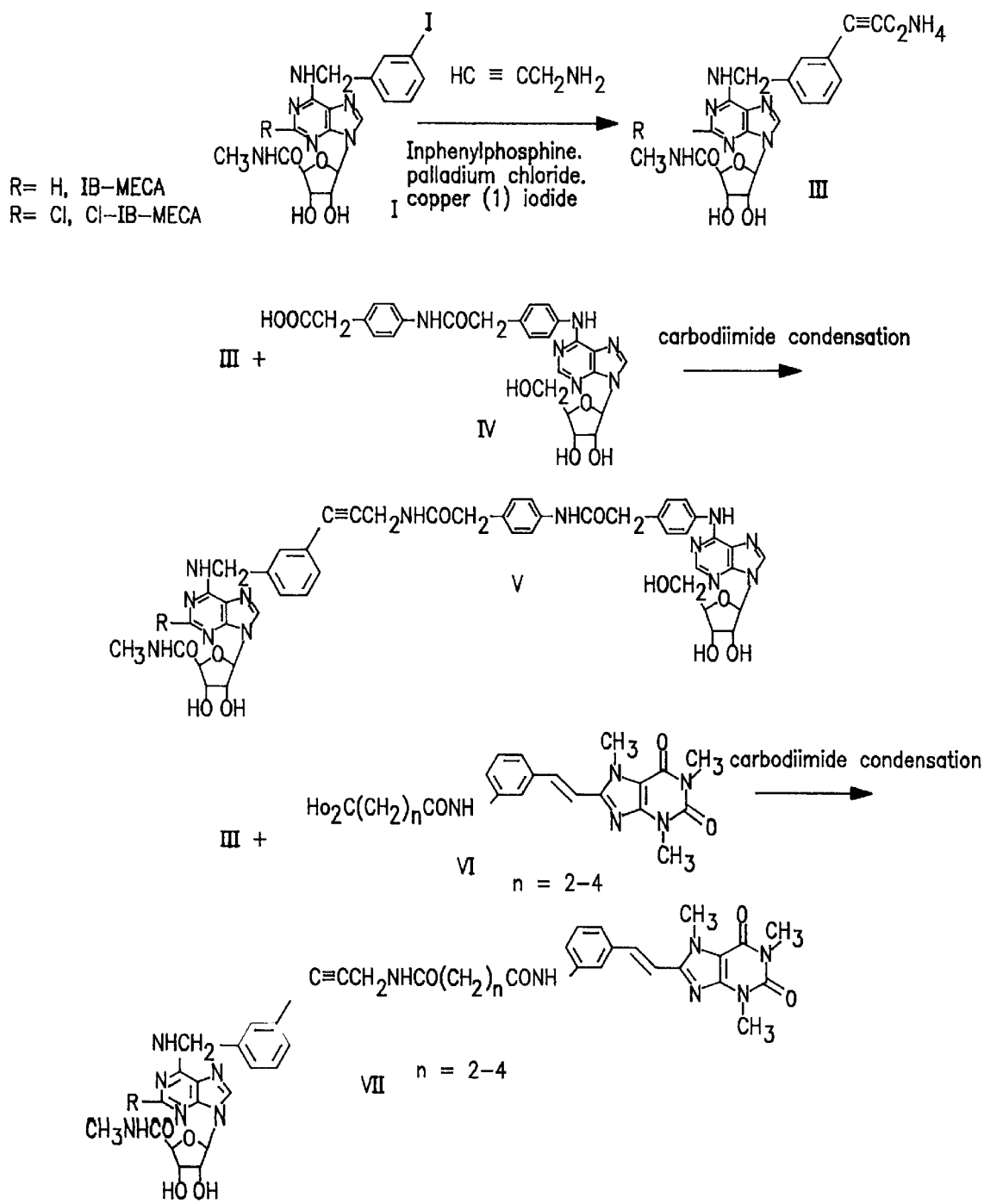
FIG. 9 is a diagram showing the synthetic scheme utilized to generate the binary compounds used in the practice of this invention.

FIG. 9 sets forth an exemplary synthetic scheme utilized to produce the binary conjugate specific for the A1 and A3 receptors.

Figure 10B:
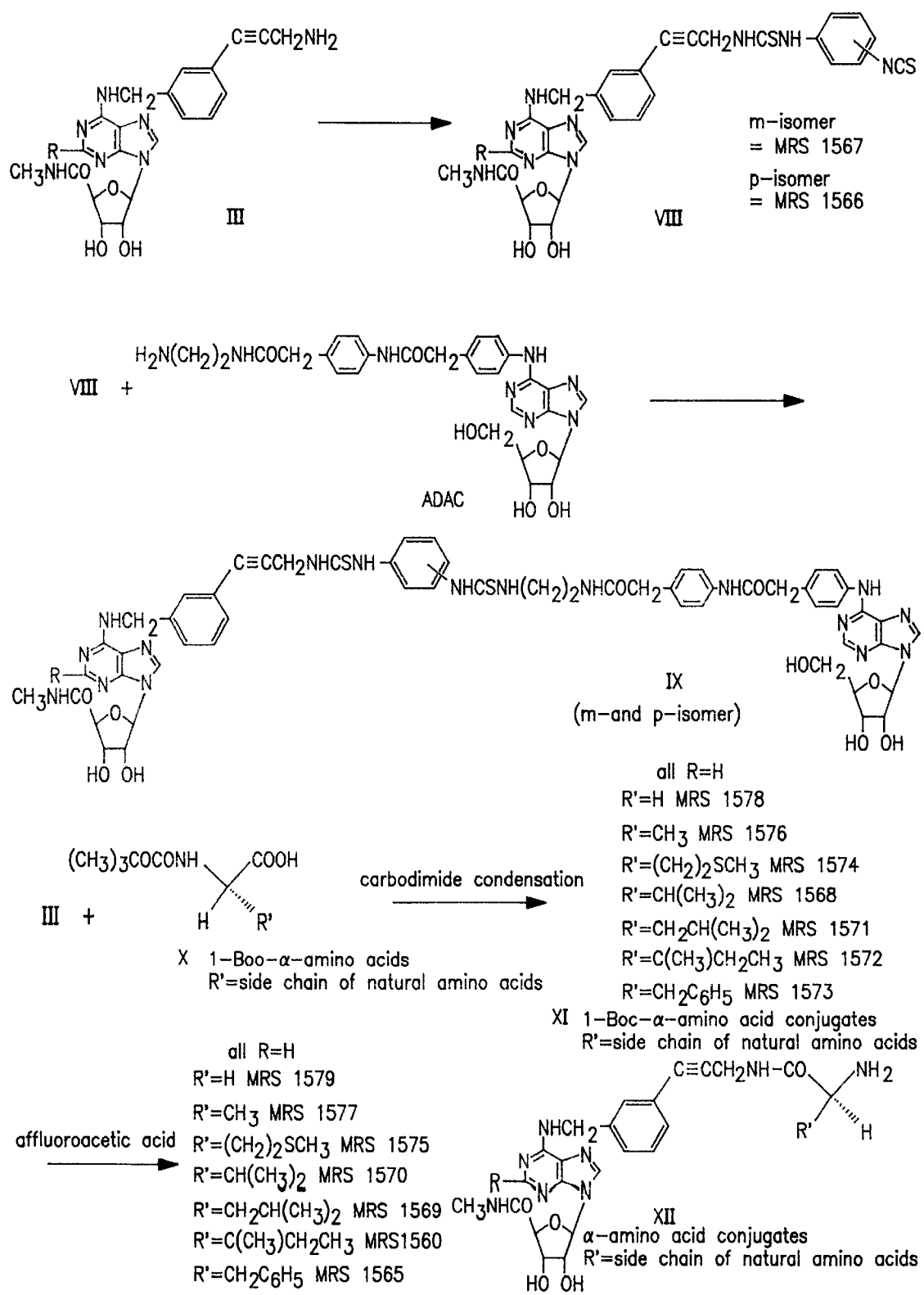
Figure 10C:
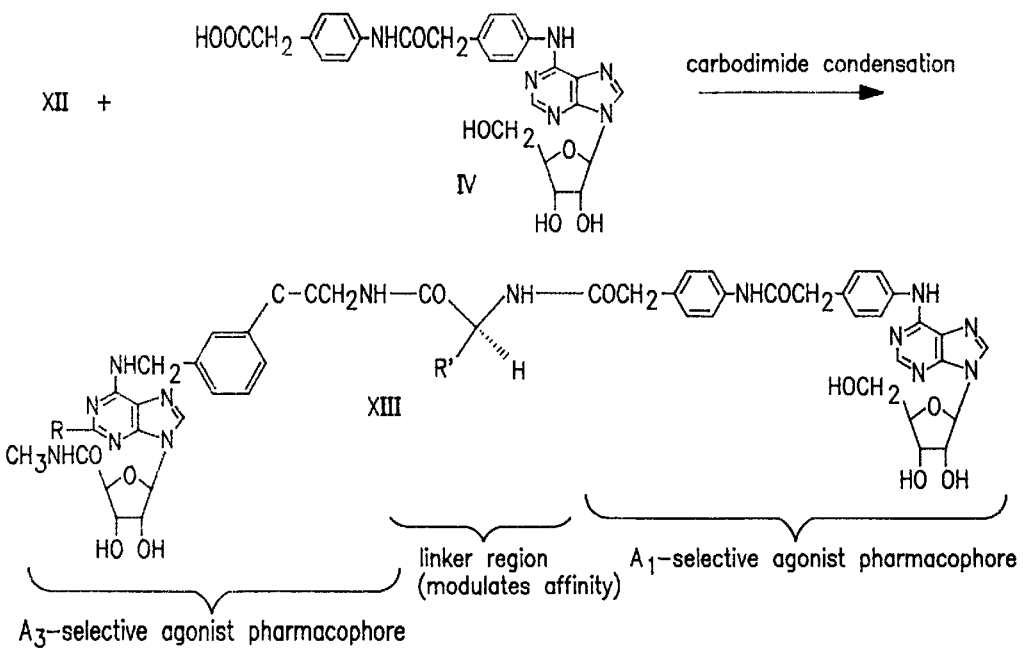
Figure 10C:
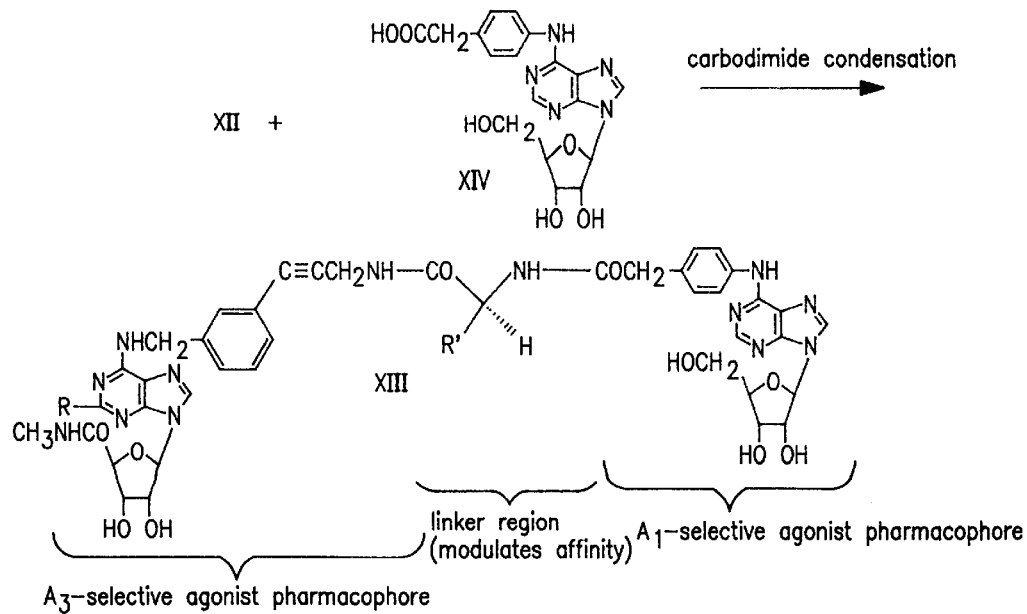

FIGS. 10A–10C depict schematic diagrams for synthesizing the compounds of the invention. FIGS. 10A–10B shows a synthetic scheme for generating a derivative of an A1 selective agonist for coupling to an amine derived A3 agonist. FIG. 10C shows a synthetic scheme for conjugating the reagents via an extended linker. Extended linkers may increase the affinity and potency of the conjugates at the adenosine receptor. Table IV lists the names of the chemical structures appearing in FIGS. 9, 10B and 10C.

TABLE IV

IB-MECA = $N^6$-(3-iodobenzyl)-5'-N-methylcarboxamidoadenosine
CompoundIII = $N^6$-[3-(3-amino-1-propynyl)benzyl]-5'-N-methylcarboxamidoadenosine TABLE IV-continued CompoundVIII (m- and p-isomers) = $N^6$-[3-[3-(3-isothiocyantophenylaminothiocarbonyl)-amino-1-propynyl]benzyl]-5'-N-methylcarboxamidoadenosine
and
$N^6$-[3-[3-(4-isothiocyanatophenylaminothiocarbonyl)-amino-1-propynyl]benzyl]-5'-N-methylcarboxamidoadenosine
ADAC = $N^6$-[4-[[[4-[[[(2-aminoethyl)amino]carbonyl]methyl]anilino]carbonyl]methyl]phenyl]adenosine
CompoundIX (m- and p-isomers) = conjugate of $N^6$-[4-[[[4-[[[(2-amino-ethyl)amino]carbonyl]methyl]anilino]carbonyl]methyl]

TABLE IV-continued phenyl]adenosine and N$^6$-[3-[3-(3-isothiocyanatophenylaminothiocarbonyl)-amino-1-propynyl]benzyl]-5'-N-methylcarboxamidoadenosine
and
conjugate of N$^6$-[4-[[[4-[[[(2-aminoethyl)amino]carbonyl]methyl]anilino]carbonyl]methyl]phenyl]adenosine and N$^6$-[3-[3-(4-isothiocyanatophenylaminothiocarbonyl)-amino-1-propynyl]benzyl]-5'-N-methylcarboxamidoadenosine
CompoundsXI =
MRS 1576 = t-Boc-L-alanyl-N$^6$-[3-(3-amino-1-propynyl)benzyl]-5'-N-methylcarboxamidoadenosine
MRS 1574 = t-Boc-L-methionyl-N$^6$-[3-(3-amino-1-propynyl)benzyl]5-'-N-methylcarboxamidoadenosine
MRS 1568 = t-Boc-L-valyl-N$^6$-[3-(3-amino-1-propynyl)benzyl]-5'-N-methylcarboxamidoadenosine
MRS 1571 = t-Boc-L-leucyl-N$^6$-[3-(3-amino-1-propynyl)benzyl]-5'-N-methylcarboxamidoadenosine
MRS 1571 = t-Boc-L-leucyl-N$^6$-[3-(3-amino-1-propynyl)benzyl]-5'-N-methylcarboxamidoadenosine
MRS 1572 = t-Boc-L-isoleucyl-N$^6$-[3-(3-amino-1-propynyl)benzyl]-5'-N-methylcarboxamidoadenosine
MRS 1573 = t-Boc-L-phenylalanyl-N$^6$-[3-(3-amino-1-propynyl)benzyl]-5'-N-methylcarboxamidoadenosine
CompoundsXII =
MRS 1577 = L-alanyl-N$^6$-[3-(3-amino-1-propynyl)benzyl]-5'-N-methylcarboxamidoadenosine
MRS 1575 = L-methionyl-N$^6$[3-(3-amino-1-propynyl)benzyl]-5'-N-methylcarboxamidoadenosine
MRS 1570 = L-valyl-N$^6$-[3-(3-amino-1-propynyl)benzyl]-5'-N-methylcarboxamidoadenosine
MRS 1569 = L-leucyl-N$^6$-[3-(3-amino-1-propynyl)benzyl]-5'-N-methylcarboxamidoadenosine
MRS 1560 = L-isoleucyl-N$^6$-[3-(3-amino-1-propynyl)benzyl]-5'-N-methylcarboxamidoadenosine
MRS 1565 = L-phenylalanyl-N$^6$-[3-(3-amino-1-propynyl)benzyl]-5'-N-methylcarboxamidoadenosine
CompoundIV = N$^6$-[4-[[[4-(carboxymethyl)anilino]carbonyl]methyl]phenyl]adenosine
CompoundXIII = conjugate of N$^6$-[4-[[[4-(carboxymethyl)anilino]anilino]carbonyl]methyl]phenyl]adenosine
and compound XII
CompoundXIV = N$^6$-[4-(carboxymethyl)phenyl]adenosine
CompoundXV = conjugate of N$^6$-[4-(carboxymethyl)phenyl]adenosine
and compound XII

EXAMPLE V

SCREENING ASSAY FOR IDENTIFYING COMPOUNDS THAT HAVE AFFINITY FOR THE A3 ADENOSINE RECEPTOR

The recombinant cardiac atrial cells described above provide a system for assessing agents that may have cardioprotective activity. A generalized method for such screening would entail providing a fixed concentration of a test compound to transfected cells and assessing whether or not the test compound exerted a protective effect during ischemia. Negative controls would comprise both untransfected cells and transfected cells not exposed to the test compound.

Once a test compound is determined to have cardioprotective activity, it will be serially diluted and applied to the transfected myocytes described above. In this way, the minimally effective concentration of the compound will be determined.

While $CaPO_4$ transfection is exemplified herein, the myocytes of the invention may be transfected using any method known to those of skill in the art. Such methods include, but are not limited to lipofectin, electroporation, or viral vector mediated transfection.

Cardiac myocytes may be transfected with any of the adenosine receptor having a known DNA sequence. Thus the assay is not limited to cells transfected with A3 encoding cDNA. Any of the known adenosine receptors may be transfected and assayed as described above. FIG. 11 shows the nucleotide sequence of the cDNA encoding the A1 adenosine receptor. FIG. 12 shows the nucleotide sequence of the cDNA encoding the A2a receptor and FIG. 13 shows the sequence of the cDNA encoding the A3 receptor (32–34).

EXAMPLE VI

ADMINSTRATION MODALITIES SUITABLE FOR THE COMPOUNDS OF THE PRESENT INVENTION

The protective effect of A3/A1 agonists has been demonstrated herein in animal models. A1/A3 agonists may be used therapeutically in patients who suffer from ischemic damage due to stable angina, unstable angina or post-myocardial infarction angina.

Several administration modalities may be utilized to treat patients with the agonists and antagonists of the invention. These modalities are influenced by bioavailability factors. For example, if the compound is metabolized in the liver or excreted in the bile, some of the active compound absorbed from the gastrointestinal tract will be inactivated by the liver before it can reach the general circulation for distribution to the site of action. It is not believed that the compounds of the invention will be subject to this first pass loss. Additionally, because the agonists of the invention are polar and water soluble, it is expected that they will have a small volume of distribution, and thus be readily eliminated by the kidney. Moreover, binding of the agonists to plasma proteins may limit their free concentrations in tissues and at their locus of action since it is only the unbound drug which equilibrates across membrane receptor sites.

Another factor affecting bioavailability is the distribution of the agonists to tissues. The agonists of the invention do not cross the blood brain barrier. Given the relatively small size of the compounds and their water solubility, it is anticipated that the compounds will have a relatively fast second phase of drug distribution. This distribution is determined by both the blood flow to the particular tissue of the organ such as the heart, as well as the rate at which the compounds diffuse into the interstitial compartment from the general circulation through the highly permeable capillary endothelium.

Patients may be perfused with the agonists of the invention by dissolving them in normal saline solution or using emulsifying agents or cosolvents followed by intravenous administration every four to six hours. Effective doses usually range from 100 to 300 nM. For example, considering a 15 liter volume of distribution for a 70 kg patient, a loading dose ranging from 0.5 to 1.5 mg is preferably used. Depending on the half-life of the agonists in the body, several doses, e.g., 1.5–4.5 mg may be adminstered per day.

Alternatively, a time-release or slow-release preparation may be utilized which allows for periodic or constant release of the antagonists over a given time period. This method would allow for a single dose of the agonists in a given day. Methods for preparing such capules are well known to those of skill in the art of drug delivery.

In summary, the present data illustrates the novel synergistic protective function of simultaneous cardiac A1 and A3 receptor activation. In addition to the synergistic role in mediating preconditioning of the cardiac myocyte, the data provide conclusive evidence that activation of both receptors can also act synergistically to attenuate myocyte injury during the prolonged injury-producing ischemia. Thus, agonists selective at the A1 and the A3 receptors represent novel potent cardioprotective agents even when ischemia has already begun. The concomitant administration of A1/A3 agonist with an A2a antagonist may also enhance cardioprotection as will binary conjugate capable of activating the A1 or A3 receptor while simultaneously blocking the A2a receptor. These data have important clinical implications in the treatment of ischemic heart disease and implicate A1 and A3 receptor-selective agonists for the reduction of the size of myocardial infarction when given during the infarct-producing ischemia.

REFERENCES

1. Babbitt, D. G., R. Virmani, and M. B. Forman. Intracoronary adenosine administered after reperfusion limits vascular injury after prolonged ischemia in the canine model. Circ. 80:1388–1399, 1989.
2. Belardinelli, L. B., J. Linden, and R. M. Berne. The cardiac effects of adenosine Prog. Cardiovasc. Dis. 32: 93–97, 1989.
3. Carr, C. S., R. J. Hill, H. Masamune, S. P. Kennedy, D. R. Knight, W. R. Tracey, and D. M. Yellon. A role for adenosine A3 receptors in ischemic preconditioning in the human atrium. Circ 94 (8): 3220, 1996.
4. Deutsch, E., M. Berger, W. G. Kussmaul, J. W. Hirshfield, H. C. Hermann, and W. K. Laskey. Adaptation to ischemia during percutaneous transluminal coronary angioplasty: Clinical, hemodynamic, and metabolic features. Circ. 82:2044–2051, 1990.
5. Downey, J. M. Ischemic preconditioning. Nature's own cardioprotective intervention. Trends Cardiovasc. Med. 2:170–176, 1992.
6. Ely, S. W., R. M. Mentzer, R. D. Lasley, B. K. Lee, and R. M. Berne. Functional and metabolic evidence of enhanced myocardial tolerance to ischemia and reperfusion with adenosine. J. Thorac. Cardiovasc. Surg. 90:549–556, 1985.
7. Ely, S. W. and R. M. Berne. Protective effects of adenosine in myocardial ischemia. Circulation 85:893–904, 1992.
8. Gallo-Rodriguez, C., X. Ji, N. Melman, B. D. Siegman, L. H. Sanders, J. Orlina, B. Fischer, Q. Pu, M. E. Olah, P. J. M. Van Galen, G. L. Stiles, and K. A. Jacobson. Structure-activity relationships of N6-benzyladenosine-5'-uronamides as A3-selective adenosine agonists. J. Med. Chem. 37:636–646, 1994.
9. Gross, G. J. ATP-sensitive potassium channels and myocardial preconditioning. Basic Res. Cardiol. 90: 85–88, 1995.
10. Hill, R. J., J. J. Oleynek, M. A. Ravi Kiron, H. Masamune, W. Weng, R. A. Buchholz, D. Knight, W. R. Tracey, R. T. Wester, and S. P. Kennedy. Cloning, expression, and pharmacological characterization of rabbit adenosine A1 and A3 receptors. J. Pharmacol. Exp. Ther. 280: 122–128, 1997.
11. Jacobson, K. A., K. L. Kirk, W. L. Padget, and J. W. Daly. Functionalized congeners of adenosine: preparation of analogues with high affinity for A1-adenosine receptors. J. Med,.Chem. 28:1341–1346, 1985.
12. Jiang, J.-L., A. M. van Rhee, N. Melman, X. D. Ji, and Jacobson, K. A. 6-phenyl-1,4-dihydropyridine derivatives as potent and selective A3 adenosine receptor antagonists. J. Med. Chem. 39: 4667–4675, 1996.
13. Kim, H. O., X. Ji, S. M. Siddiqi, M. E. Olah, G. L. Stiles, and K. A. Jacobson. 2-Substitution of N6-benzyladenosine-5'-uronamides enhances selectivity for A3 adenosine receptors. J. Med. Chem. 37:3614–3621,1994.
14. Li, G. C., J. A. Vasquez, K. P. Gallagher, and B. R. Lucchesi. Myocardial protection with preconditioning. Circ. 82:609–619, 1990.
15. Liang, B. T. Adenosine receptors and cardiovascular function. Trends in Cardiovascular Medicine 2:100–108, 1992.
16. Liang, B. T. Direct preconditioning of cardiac ventricular myocytes via adenosine A1 receptor and KATP channel. Amecian J. Physiol. 271 (Heart Circ. Physiol. 40): H1769–H1777, 1996.
17. Miura, T., T. Ogawa, T. Iwamoto, K. Shimamoto, and O. Iimura. Dipyridamole potentiates the myocardial infarct size-limiting effect of ischemic preconditioning. Circ. 86:979–985, 1992.
18. Murry, C. E., R. B. Jennings, and K. A. Reimer. Preconditioning with ischemia: A delay of lethal cell injury in ischemic myocardium. Circ. 74:1124–1136, 1986.
19. Olafsson, B., M. B. Forman, D. W. Puett, A. Pou, C. U. Cates. Reduction of reperfusion injury in the canine preparation by intracoronary adenosine: Importance of the endothelium and the no-reflow phenomenon. Circ. 76:1135–1145, 1987.
20. Olsson, R. A. and J. D. Pearson. Cardiovascular purinoceptors. Physiol. Rev. 70: 761–809, 1990.
21. Reibel, D. K., and M. J. Rovetto. Myocardial ATP synthesis and mechanical function following oxygen deficiency. Am. J. Physiol. 234: H620–H624, 1978.
22. Reibel, D. K., and M. J. Rovetto. Myocardial adenosine salvage rates and restoration of ATP content following ischemia. Am. J. Physiol. 237: H247–H252, 1979.
23. Strickler, J., K. A. Jacobson, and B. T. Liang.: Direct preconditioning of cultured chick ventricular myocytes: Novel functions of cardiac adenosine A2a and A3 receptors. J. Clin. Invest. 98: 1773–1779, 1996.
24. Tracey, W. R., R. J. Hill, A. H. Smith, F. W. Bangerter, J. T. McAndrew, S. P. Kennedy, H. Masamune, R. T. Wester, and R. A. Buchholz. Selective adenosine A3 receptor stimulation reduces ischemic myocardial injury in the rabbit heart. Circ 94 (8): 3218, 1996.
25. Wyatt, D. A., S. W. Ely, R. D. Lasley, R. Walsh, R. Mainwaring, R. M. Berne, and R. M. Mentzer. Purine-enriched asanguineous cardioplegia retards adenosine triphosphate degradation during ischemia and improves post ischemic ventricular function. J. Thorac. Cardiovasc. Surg. 97:771–778, 1989.
26. Zhou, Q. Y., C. Li, M. E. Olah, R. A. Johnson, G. L. Stiles, and O. Civelli. Molecular cloning and characterization of an adenosine receptor: The A3 adenosine receptor. Proc. Natl. Acad. Sci. USA 89:7432–7436, 1992.

27. Baraldi, P. G., B. Cacciari, G. Spalluto, X. Ji, M. E. Olah, G. Stiles, S. Dionisotti, C. Zocchi, E. Ongini, and K. Jacobson. Novel N6-(Substituted-phenylcarbamoyl) adenosine-5'uronamides as Potent Agonists for A3 Adenosine Receptors. J. Med. Chem. 39:802–806, 1996.
28. Siddiqi, S. M., R. A. Pearlstein, L. H. Sanders, and K. A. Jacobson. Comparative Molecular Field Analysis of Selective A3 Adenosine Receptor Agonists. Biorganic and Medicinal Chemistry. 3:1331–1343, 1995.
29. Van Galen, P. J. M., A. H. Van Bergen, C. Gallo-Rodriguez, N. Melman, M. E. Olah, A. P. IJzerman, G. L. Stiles, and K. A. Jacobson. A Binding Site Model and Structure-Activity Relationships for the Rat A3 Adenosine Receptor. Mol. Pharmacology 45:1101–1111, 1994.
30. Jacobson, K. A., Kim, H. O., Siddiqi, S. M., Olah, M. E., Stiles, G., and von Lubitz, D. K. J. E. A3 adenosine receptors: design of selective ligands and therapeutic agents. Drugs of the Future. 20:689–699, 1995.
31. Jacobson, K. A., Gallo-Rodriquez, C., Melman, N., Fischer, B., Maillard, M., van Bergen, A., van Galen, P. J., Karton, Y. Structure-Activity Relationships of 8-Stryrylxanthines as A2-Selective Adenosine Antagonists. J. Med. Chem. 36:1333–1342, 1992.
32. Furlong, T. J., et al., Molecular Characterization of a human brain adenosine A2 receptor. Molecular Brain Research 15:62–66, 1992.
33. Townsend-Nicholson, A., et al. Molecular Cloning and characterization of a human brain A1 adenosine receptor cDNA. Mol. Brain Res. 16:365–370, 1997.
34. Atkinson, M., et al., Cloning, characterization and chromosomal assignment of the human adenosine A3 receptor gene. Neurosci. Res. 29:73–79, 1997.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for preventing or reducing ischemic damage to the heart, in a patient in need thereof, comprising administering to said patient an agonist having affinity for both the A1 and A3 adenosine receptors in an amount effective to activate A3 and A1 receptors in the heart of said patient.

2. A method as claimed in claim 1, wherein said agonist is delivered using an administration means selected from the group consisting of intravenous administration, oral administration and cardiac perfusion.

3. A method as claimed in claim 1, wherein said agonist is selected from the group of compounds listed in Table II.

4. A method as claimed in claim 1, wherein said agonist is $N^6$-((2-trifluoromethyl)carbamoyl) adenosine-5'uronamide.

5. A method as claimed in claim 1, wherein said agonist is $N^6$-((3-iodophenyl)carbamoyl)adenosine-5'uronamide.

6. A method as claimed in claim 1 wherein said agonist is a binary conjugate which has affinity for, and activates the A1 and A3 adenosine receptors simultaneously.

7. A method as claimed in claim 1 wherein said agonist is administered to said patient prior to a surgical procedure having potential to cause cardiac ischemic damage.

8. A method as claimed in claim 1, wherein said agonist is administered to said patient during a surgical procedure having potential to cause cardiac ischemic damage.

9. A method as claimed in claim 1, wherein said agonist is administered to said patient following a surgical procedure having potential to result in cardiac ischemic damage.

10. A method as claimed in claim 1, wherein said patient is in need of said treatment due to an anginal condition selected from the group consisting of chronic stable angina, unstable angina, post myocardial infarction angina.

11. A method as claimed in claim 1, wherein said patient is in need of such treatment due to acute myocardial infarction.

12. A method for preventing or reducing ischemic damage to the heart, in a patient in need thereof, comprising administering to said patient an mixed agonist having affinity for the A3 and A1 adenosine receptors and an antagonist having affinity for the A2a adenosine receptor in amounts effective to activate said A3 and A1 receptors and inhibit activation of said A2a receptor in the heart of said patient.

13. A method as claimed in claim 12, wherein said agonist and said antagonist are delivered using an administration means selected from the group consisting of intravenous administration, oral administration and cardiac perfusion.

14. A method as claimed in claim 12, wherein said agonist is selected from the group consisting of $N^6$-((3-iodophenyl)carbamoyl)adenosine-5'uronamide, $N^6$-((2-trifluoromethyl)carbamoyl)adenosine-5'uronamide, $N^6$-(4-nitrobenzyl)adenosine-5'-N-ethyluronamide, 6-(O-henylhydroxyamino purine-9-beta-ribofuranoside-5'-N-methyluronamide, $N^6$-cyclohexyl-5'-N-ethylcarboxamido)adensine, and $N^6$-[4-[[[4-[2-aminoethyl)amino]carbonyl]methyl]-anilino]carbonyl]methyl]phenyl]adenosine.

15. A method as claimed in claim 12 wherein said antagonist is selected from the group of 8 styrylxanthine derivative compounds listed in Table III consisting of compounds 15b, 17b, 19b, 20b, 21b, 22b, 23, 24, 25, 26, 27b, 28, 29b, 32b, 33a, 33b, 34b, 35, 36, 37, 38, 39, 40, 41, 42, 43b, 44b, 45b, 46, 51b, 52b, 53b.

16. A method as claimed in claim 12, wherein said agonist is $N^6$-((2-trifluoromethyl)carbamoyl)adenosine-5'uronamide.

17. A method as claimed in claim 12, wherein said agonist is $N^6$-((3-iodophenyl)carbamoyl)adenosine-5'uronamide.

18. A method as claimed in claim 12, wherein said agonist is selected from the group consisting of MRS 584, MRS 479, MRS 537 or MRS 1340.

19. A method as claimed in claim 12, wherein said antagonist is selected from the group consisting of CSC, DMPX, ZM241385 or SCH58261.

20. A method as claimed in claim 12, wherein said agonist and said antagonist are administered to said patient prior to a surgical procedure having potential to cause cardiac ischemic damage.

21. A method as claimed in claim 12, wherein said agonist and said antagonist are administered to said patient during a surgical procedure having potential to cause cardiac ischemic damage.

22. A method as claimed in claim 12, wherein said agonist and said antagonist are administered to said patient following a surgical procedure having potential to result in cardiac ischemic damage.

23. A method as claimed in claim 12, wherein said patient is in need of said treatment due to an anginal condition selected from the group consisting of chronic stable angina, unstable angina, and post myocardial infarction angina.

24. A method as claimed in claim 12, wherein said patient is in need of said treatment due to acute myocardial infarction.

25. A method for preventing or reducing ischemic damage to the heart, in a patient in need thereof, comprising administering to said patient a binary conjugate, which acts as an adenosine A3 receptor agonist while simultaneously inhibiting the activation of A2a receptors in an amount effective to enhance myocardial response to said preconditioning stimuli.

26. A method as claimed in claim 25, wherein said patient is in need of such treatment due to a cardiac condition selected from the group consisting of chronic stable angina, unstable angina, post-myocardial infarction angina or acute myocardial infarction.

27. A method as claimed in claim 25 wherein said agonist is administered to said patient prior to a surgical procedure which may cause cardiac ischemic damage.

28. A method as claimed in claim 25, wherein said agonist is administered to said patient during a surgical procedure having potential to cause cardiac ischemic damage.

29. A method as claimed in claim 25, wherein said agonist is administered to said patient following a surgical procedure which may result in cardiac ischemic damage.

30. A method for preventing or reducing ischemic damage to the heart, in a patient in need thereof, comprising administering to said patient both an adenosine A3 receptor agonist and at least one adenosine A1 receptor agonist in an amount effective to activate the A1 and A3 adenosine receptors in the heart of said patient.

31. A method as claimed in claim 30, wherein said agonists are delivered using an administration means selected from the group consisting of intravenous administration, oral administration and cardiac perfusion.

32. A method as claimed in claim 30, wherein said agonist and said agonists are administered to said patient prior to a surgical procedure having potential to cause cardiac ischemic damage.

33. A method as claimed in claim 30, wherein said agonist and said antagonist are administered to said patient during a surgical procedure having potential to cause cardiac ischemic damage.

34. A method as claimed in claim 30, wherein said agonist and said antagonist are administered to said patient following a surgical procedure having potential to result in cardiac ischemic damage.

35. A method as claimed in claim 30, wherein said patient is in need of said treatment due to an anginal condition selected from the group consisting of chronic stable angina, unstable angina, and post myocardial infarction angina.

36. A method as claimed in claim 30, wherein said patient is in need of said treatment due to acute myocardial infarction.

37. A method as claimed in claim 30, wherein said A3 agonist is selected from the group of compounds consisting of IB-MECA, Cl-IB-MECA, MRS 584, MRS 479, MRS 537, MRS 1340, and DBXMR and said A1 agonist is selected from the group of compounds listed in Table I consisting of CPA, CCPA, ADAC R-PIA, SPA, CHA, SDZWAG 994 and NNC21-0136.

38. A binary conjugate for preventing or reducing ischemic damage to the heart, said conjugate acting as an agonist at the A3 adenosine receptor and an antagonist at the A2a adenosine receptor.

39. A binary conjugate as claimed in claim 38, said conjugate having the structure of MRS 1528.

40. A method for administering the binary conjugated of claim 38, wherein said conjugate is delivered using an administration means selected from the group consisting of intravenous administration, oral administration and cardiac perfusion.

41. A method as claimed in claim 40, wherein said conjugate is administered to said patient prior to a surgical procedure having potential to cause cardiac ischemic damage.

42. A method as claimed in claim 40, wherein said conjugate is administered to said patient during a surgical procedure having potential to cause cardiac ischemic damage.

43. A method as claimed in claim 40, wherein said conjugate is administered to said patient following a surgical procedure having potential to result in cardiac ischemic damage.

44. A method as claimed in claim 40, wherein said patient is in need of said treatment due to an anginal condition selected from the group consisting of chronic stable angina, unstable angina, and post myocardial infarction angina.

45. A method as claimed in claim 40, wherein said patient is in need of said treatment due to acute myocardial infarction.

46. A binary conjugate for preventing or reducing ischemic damage to the heart, said conjugate acting as an agonist at the A3 adenosine receptor and an agonist at the A1 adenosine receptor.

47. A binary conjugate as claimed in claim 46, said conjugate being selected from the group of compounds consisting of i) MRS1543, ii) a conjugate of $N^6$-[4-[[[4-(carboxymethyl)anilino]anilino]carbonyl]methyl]phenyl]adenosine and L-glycyl-$N^6$-[3-(3-amino-1-propynyl)benzyl]-5'-N-methylcarboxamidoadenosine, iii) a conjugate of $N^6$-[4-[[[4-(carboxymethyl)anilino]anilino]carbonyl]methyl]phenyl]adenosine and L-alanyl-$N^6$-[3-(3-amino-1-propynyl)benzyl]-5'-N-methylcarboxamidoadenosine, iv) a conjugate of $N^6$-[4-[[[4-(carboxymethyl)anilino]anilino]carbonyl]methyl]phenyl]adenosine and L-methionyl-$N^6$-[3-(3-amino-1-propynyl)benzyl]-5'-N-methylcarboxamidoadenosine, v) a conjugate of $N^6$-[4-[[[4-(carboxymethyl)anilino]anilino]carbonyl]methyl]phenyl]adenosine and L-valyl-$N^6$-[3-(3-amino-1-propynyl)benzyl]-5'-N-methylcarboxamidoadenosine, vi) a conjugate of $N^6$-[4-[[[4-(carboxymethyl)anilino]anilino]carbonyl]methyl]phenyl]adenosine and L-leucyl-$N^6$-[3-(3-amino-1-propynyl)benzyl]-5'-N-methylcarboxamidoadenosine, vii) a conjugate of $N^6$-[4-[[[4-(carboxymethyl)anilino]anilino]carbonyl]methyl]phenyl]adenosine and L-isoleucyl-$N^6$-[3-(3-amino-1-propynyl)benzyl]-5'-N-methylcarboxamidoadenos viii) a conjugate of $N^6$-[4-[[[4-(carboxymethyl)anilino]anilino]carbonyl]methyl]phenyl]adenosine and L-phenylalanyl-$N^6$-[3-(3-amino-1-propynyl)benzyl]-5'-N-methylcarboxamidoadenosine.

48. A binary conjugate as claimed in claim 46, said conjugate being selected from the group of compounds consisting of i) a conjugate of $N^6$-[4-(carboxymethyl)phenyl]adenosine and L-glycyl-$N^6$-3-(3-amino-1-propynyl)benzyl]-5'-N-methylcarboxamidoadenosine, ii) a conjugate of $N^6$-[4-(carboxymethyl)phenyl]adenosine and L-alanyl-$N^6$-[3-(3-amino-1-propynyl)benzyl]-5'-N-methylcarboxamidoadenosine, iii) a conjugate of $N^6$-[4-(carboxymethyl)phenyl]adenosine and $Ch_3$]L-methionyl-$N^6$-[3-(3-amino-1-propynyl)benzyl]-5'-N-methylcarboxamidoadenosine, iv) a conjugate of $N^6$-[4-(carboxymethyl)phenyl]adenosine and L-valyl-$N^6$-[3-(3-amino-1-propynyl)benzyl]-5'-N-methylcarboxamidoadenosine, v) a conjugate of $N^6$-[4-(carboxymethyl)phenyl]adenosine and L-leucyl-$N^6$-[3-(3-amino-1-propynyl)benzyl]-5'-N-methylcarboxamidoadenosine, vi) a conjugate of $N^6$-[4-(carboxymethyl)phenyl]adenosine and L-isoleucyl-$N^6$-[3-(3-amino-1-propynyl)benzyl]-5'-N-methylcarboxamidoadenosine, vii) a conjugate of $N^6$-[4-(carboxymethyl)phenyl]adenosine and L-phenylalanyl-$N^6$-[3-(3-amino-1-propynyl)benzyl]-5'-N-methylcarboxamidoadenosine.

49. A method for administering the binary conjugated of claim 46, wherein said conjugate is delivered using an administration means selected from the group consisting of intravenous administration, oral administration and cardiac perfusion.

50. A method as claimed in claim 49, wherein said conjugate is administered to said patient prior to a surgical procedure having potential to cause cardiac ischemic damage.

51. A method as claimed in claim 49, wherein said conjugate is administered to said patient during a surgical procedure having potential to cause cardiac ischemic damage.

52. A method as claimed in claim 49, wherein said conjugate is administered to said patient following a surgical procedure having potential to result in cardiac ischemic damage.

53. A method as claimed in claim 49, wherein said patient is in need of said treatment due to an anginal condition selected from the group consisting of chronic stable angina, unstable angina, and post myocardial infarction angina.

54. A method as claimed in claim 49, wherein said patient is in need of said treatment due to acute myocardial infarction.

55. A recombinant cardiac myocyte comprising nucleic acid molecules encoding two or more adenosine receptors selected from the group consisting of the A1 receptor, the A3 receptor, and the A2a receptor.

56. A recombinant myocyte as claimed in claim 55, whrerein the myocyte is a chick embryo ventricular myocyte and the adenosine receptor is a human adenosine receptor.

57. A method for determining whether a test compound exerts a cardioprotective effect, comprising:
   a) providing a recombinant myocyte expressing an adenosine receptor as claimed in claim 55;
   b) contacting said cells with said test compound;
   c) exposing cells to ischemic conditions; and
   d) assessing the presence of said cardioprotective effect, if any, exerted by said test compound.

58. A method as claimed in claim 57, wherein said cardioprotective effect is assessed by determining the number of myocytes killed.

59. A method as claimed in claim 57, wherein said cardioprotective effect is assessed by determining the amount of creatine kinase released from said recombinant cardiac myocytes.

60. A method as claimed in claim 57, wherein said recombinant myocyte is selected from the group consisting of chick embryo ventricular myocytes or adult rat ventricular myocytes.

* * * * *